(12) United States Patent
Yoshikawa et al.

(10) Patent No.: US 10,738,101 B2
(45) Date of Patent: Aug. 11, 2020

(54) METHOD FOR SELECTING ODOR-CONTROLLING SUBSTANCE

(71) Applicant: Kao Corporation, Tokyo (JP)

(72) Inventors: Keiichi Yoshikawa, Saitama (JP); Naoko Saito, Utsunomiya (JP)

(73) Assignee: Kao Corporation, Tokyo (JP)

( * ) Notice: Subject to any disclaimer, the term of this patent is extended or adjusted under 35 U.S.C. 154(b) by 63 days.

(21) Appl. No.: 15/576,514

(22) PCT Filed: May 27, 2016

(86) PCT No.: PCT/JP2016/065656
§ 371 (c)(1),
(2) Date: Nov. 22, 2017

(87) PCT Pub. No.: WO2016/194788
PCT Pub. Date: Dec. 8, 2016

(65) Prior Publication Data
US 2018/0127482 A1    May 10, 2018

(30) Foreign Application Priority Data

May 29, 2015 (JP) ................................ 2015-110390
May 12, 2016 (JP) ................................ 2016-096146

(51) Int. Cl.
| | |
|---|---|
| G01N 33/53 | (2006.01) |
| G01N 33/554 | (2006.01) |
| G01N 33/566 | (2006.01) |
| C07K 14/705 | (2006.01) |
| A61B 5/00 | (2006.01) |

(52) U.S. Cl.
CPC ...... *C07K 14/70571* (2013.01); *A61B 5/4011* (2013.01); *C07K 14/705* (2013.01); *G01N 33/53* (2013.01); *G01N 33/566* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2002/0046710 | A1 | 4/2002 | Preti et al. |
| 2007/0020210 | A1 | 1/2007 | Preti et al. |
| 2013/0216492 | A1 | 8/2013 | Kato et al. |
| 2014/0186864 | A1 | 7/2014 | Kato et al. |
| 2015/0110731 | A1 | 4/2015 | Namba et al. |

FOREIGN PATENT DOCUMENTS

| | | | |
|---|---|---|---|
| JP | 2005-053887 | A | 3/2005 |
| JP | 2008-304445 | A | 12/2008 |
| JP | 2012-050781 | A | 3/2012 |
| JP | 4966790 | A | 4/2012 |
| JP | 5646255 | B | 11/2014 |
| JP | 2014-235098 | A | 12/2014 |
| WO | WO 2012/029922 | A1 | 3/2012 |
| WO | WO 2012/169644 | A1 | 12/2012 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
International Search Report (ISR) for PCT/JP2016/065656; I.A. fd May 27, 2016, dated Aug. 30, 2016 from the Japan Patent Office, Tokyo, Japan.
International Preliminary Report on Patentability (IPRP), Chapter 1 of the Patent Cooperation Treaty, including the Written Opinion for PCT/JP2016/065656; I.A. fd May 27, 2016, dated Dec. 5, 2017, by the International Bureau of WIPO, Geneva, Switzerland.
Shirasu, M et al., "Olfactory receptor and neural pathway responsible for highly selective sensing of musk odors," Neuron. Jan. 8, 2014;81(1):165-78. doi: 10.1016/j.neuron.2013.10.021. Epub Dec. 19, 2013, Cell Press, Cambridge, MA.
Mainland, JD et al., "The missense of smell: functional variability in the human odorant receptor repertoire," Nat Neurosci. Jan. 2014;17(1):114-20. doi: 10.1038/nn.3598. Epub Dec. 8, 2013, Nature America Inc, New York, NY.
Kawasaki, M et al.,, "Kyukaku to Nioi Busshitsu (Olfactory and Odorous Substances," section 4.1.3, pp. 71-72, Japan Association on Odor Environment, 1998.
Pierce, JD et al., "The Role of Perceptual and Structural Similarity in Cross-adaptation," Chem Senses. Apr. 1996;21(2):223-37, Oxford University Press, Oxford, England.
Kurtz, AJ et al., "The Cross-Adaptation of Green and Citrus Odorants," Chemosensory Perception (Dec. 2010) 3(3-4):149-155, first online: Aug. 17, 2010, Springer, New York, NY.
Extended European Search Report including the supplementary European search report and the European search opinion, for EP Appl. No. 16803223.3, dated Oct. 11, 2018, European Patent Office, Munich, Germany.
Pierce, JD et al., "Cross-adaptation of sweaty-smelling 3-methyl-2-hexenoic acid by a structurally-similar, pleasant-smelling odorant," Chem Senses. Aug. 1995;20(4):401-11, Oxford University Press, Oxford, England.

* cited by examiner

Primary Examiner — Joanne Hama
Assistant Examiner — Jon M Lockard
(74) *Attorney, Agent, or Firm* — Sterne, Kessler, Goldstein & Fox P.L.L.C.

(57) ABSTRACT

A method for searching for a substance suppressing a target odor through cross-adaptation is provided. A method for selecting a substance inducing cross-adaptation of a target odor includes: searching olfactory receptor polypeptides to identify an olfactory receptor polypeptide responding to a causative substance of the target odor; adding a test substance, which is different from the causative substance of the target odor, to the identified olfactory receptor polypeptide to measure response thereof; and selecting the test substance which activates the response of the olfactory receptor polypeptide as the substance inducing the cross-adaptation of the target odor.

22 Claims, 6 Drawing Sheets

Specification includes a Sequence Listing.

[Figure 1]
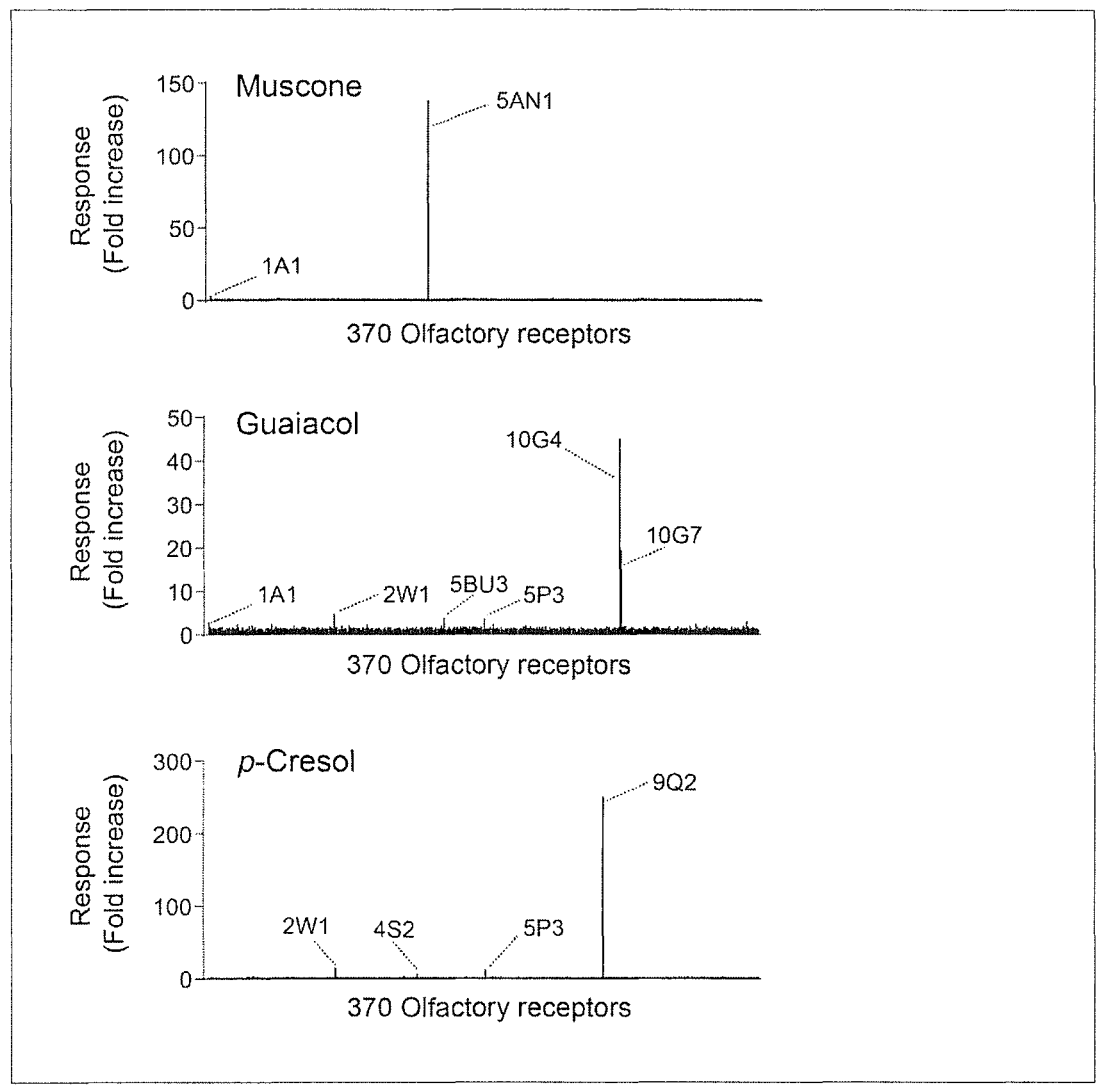

[Figure 2]
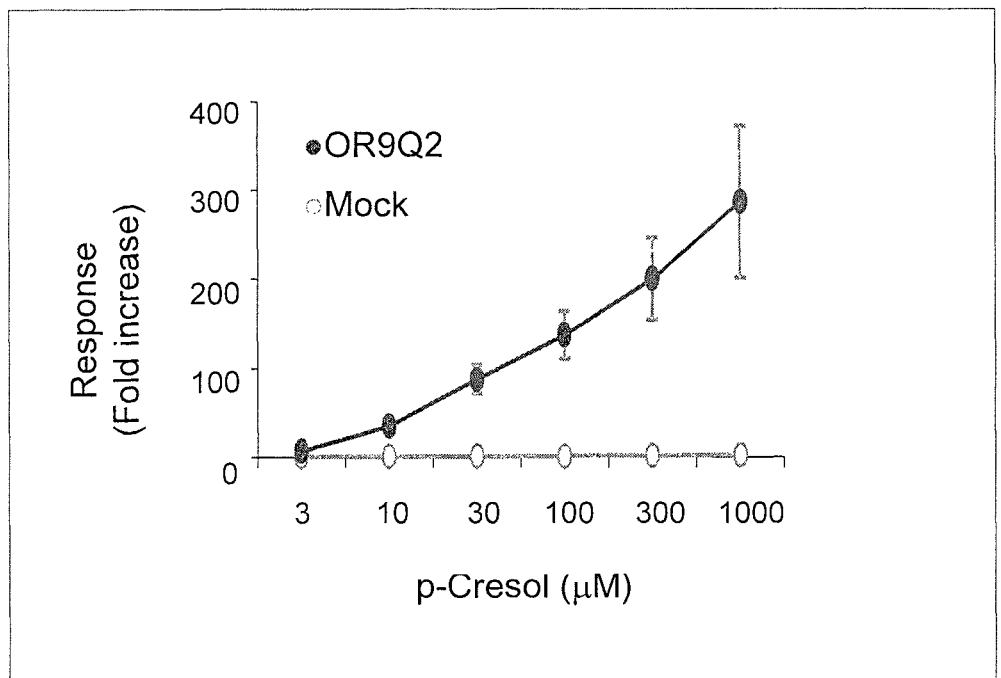

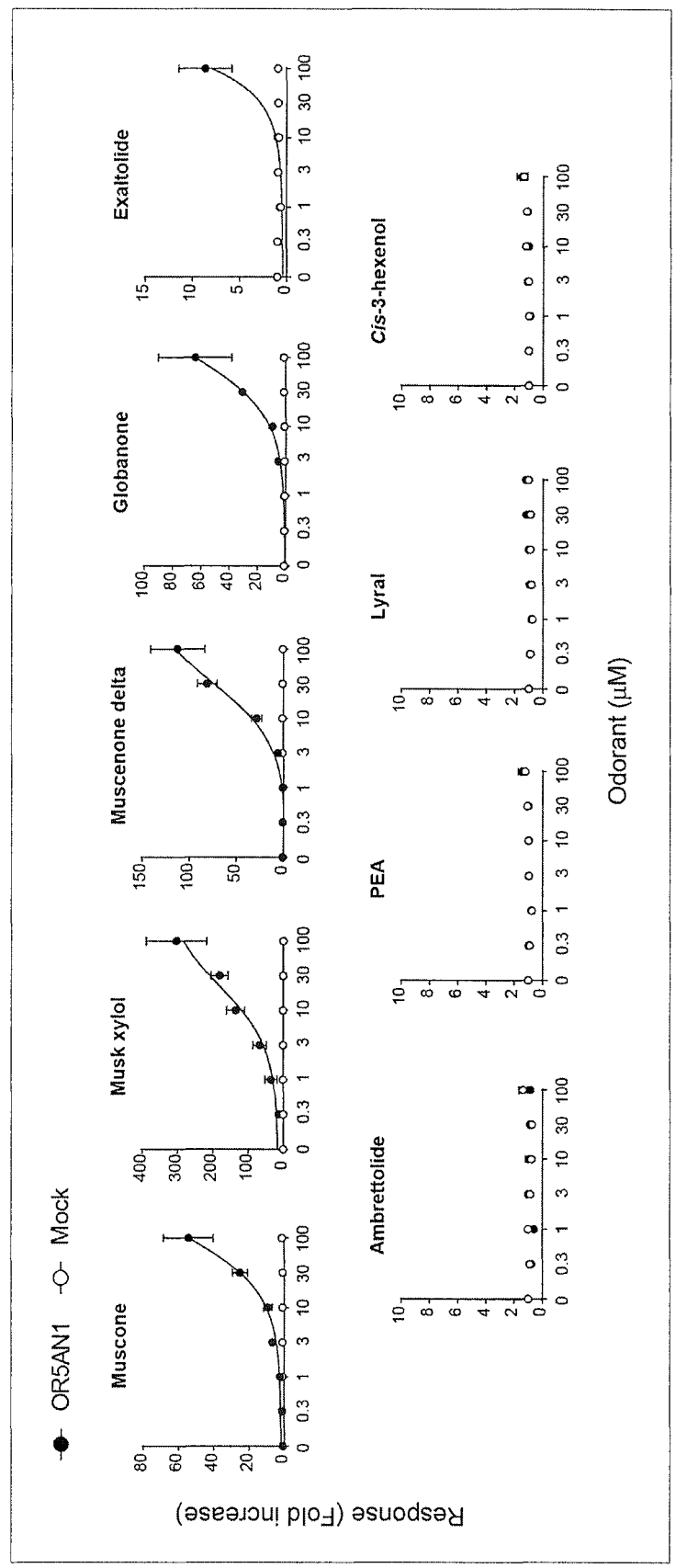
[Figure 3]

[Figure 4]
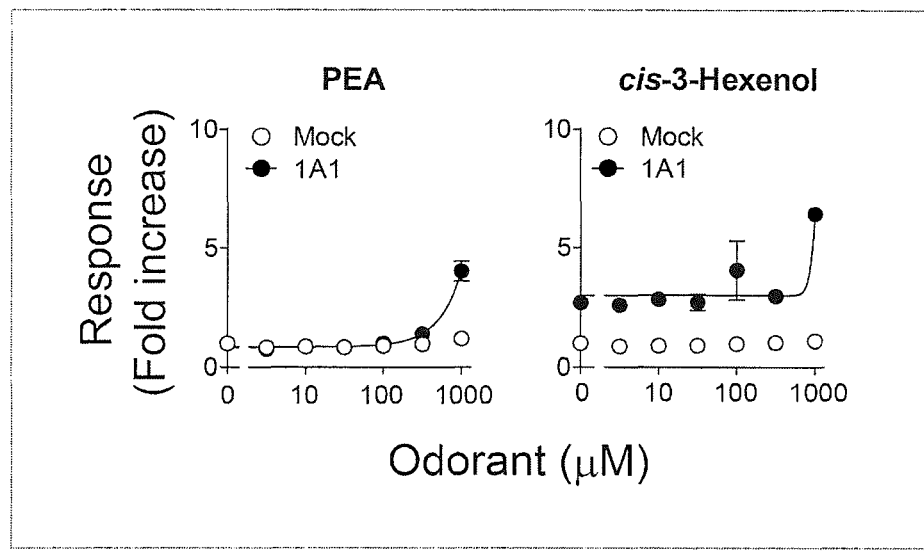

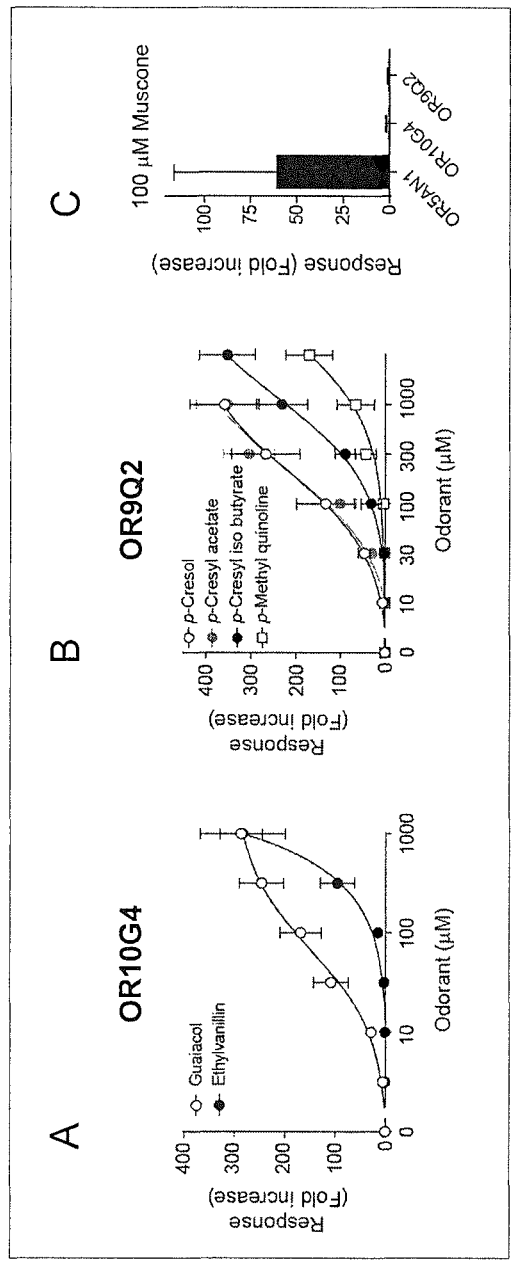
[Figure 5]

[Figure 6]
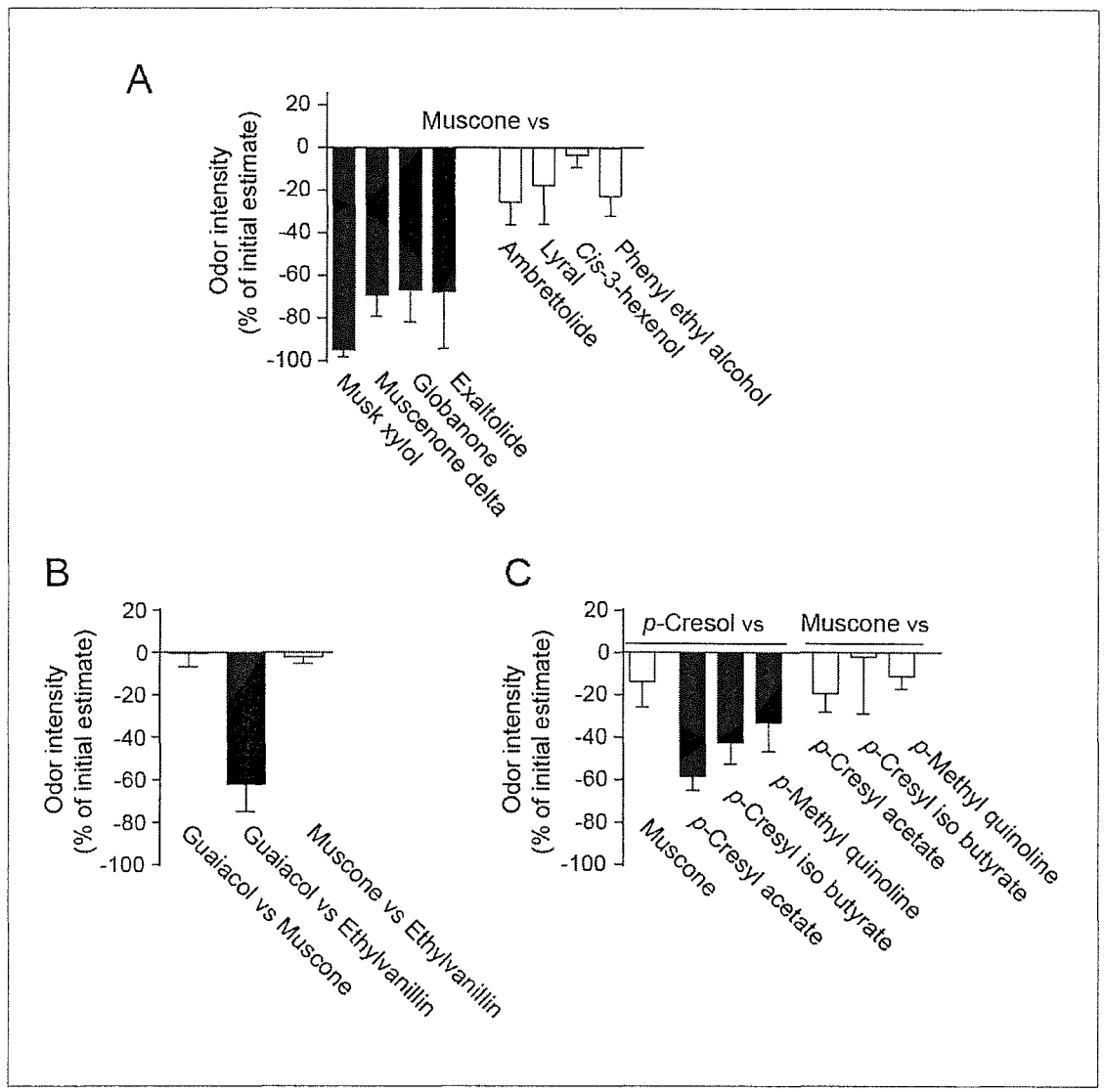

METHOD FOR SELECTING ODOR-CONTROLLING SUBSTANCE

FIELD OF THE INVENTION

The present invention relates to a method for suppressing an odor on the basis of a mechanism for olfactory adaptation.

BACKGROUND OF THE INVENTION

In a mammal such as a human, an odorous substance is recognized by an olfactory receptor of an olfactory neuron present in olfactory epithelium spread in the deepest portion of a nasal cavity. An odor molecule taken into the nasal cavity works on and activates the olfactory receptor (OR), and a signal from the olfactory sensory neuron caused by the activated olfactory receptor is transmitted to the central nervous system, and thus, an odor is perceived. As for a human, it is presumed that there are 400 or more genes encoding olfactory receptors. It is regarded that the odor quality perceived by a human from a specific odorous substance is determined depending on which combination of 400 or more olfactory receptors is activated.

There are already a variety of reports on the relationship between an odor and olfactory receptors relating to the recognition of the odor. For example, it is suggested, through studies using a mouse made in 2014, that a musk odor which is one of several hundred thousand odorous substances, is recognized exceptionally by a very small number of olfactory receptors. As for a human, merely one olfactory receptor OR5AN1 has been found as the olfactory receptor recognizing musk, and it is suggested that this one receptor makes a large contribution to the recognition of the musk odor (Non Patent Literature 1). Besides, it is suggested that, for example, one olfactory receptor designated as OR10G4 makes a large contribution to recognition of an odorous substance designated as guaiacol (2-methoxyphenol) (Non Patent Literature 2).

In accordance with recent increase in attention to hygiene, various offensive odors, such as a "musty odor" generated in textile products such as clothes, "body odors" generated from the head, the mouth, the groin, the sole and the like, and a "urine odor" generated from urine excreted a long time ago, have become a problem. Many of odorous substances corresponding to causes of these offensive odors are volatile low molecular weight organic compounds having a molecular weight of about 30 to 300. As a method for reducing discomfort against an offensive odor, chemical deodorization utilizing a neutralization reaction, physical deodorization of adsorbing an offensive odorous substance to a porous surface or the like, or sensuous deodorization utilizing a different odorous substance may be employed. Examples of the sensuous deodorization include (1) a method in which another odorous substance is introduced into an environment of an offensive odor to be smelled together with the offensive odor (masking), and (2) a method in which olfactory sensitivity of a human to an offensive odor is lowered by causing another odorous substance to be smelled before smelling the offensive odor (cross-adaptation).

In recent years, efforts have been made to find out an olfactory mechanism of causing sensuous deodorization for efficiently developing a sensuous deodorization technique based on the finding. For example, it has been reported that an odor molecule activating a given olfactory receptor works as an antagonist to inhibit activation of another olfactory receptor. On the basis of this fact, a technique utilizing an antagonist of an olfactory receptor recognizing an offensive odor has been reported as a kind of the sensuous deodorization (1) by masking (Patent Literature 1). Currently, this technique utilizing an antagonist is the only one sensuous deodorization technique from the viewpoint of directly controlling an olfactory receptor.

The method of the sensuous deodorization (2) is a method on the basis of a physiological phenomenon of the olfactory cross-adaptation. The olfactory cross-adaptation is defined as a reduction in sensitivity to an odorant due to habituation to a different odorant following habituation to an odorant. In other words, when one is caused to get used to an odor not offensive, he/she gets used to an offensive odor and hence his/her perception is suppressed. Patent Literature 2 describes an odor-suppressing method based on the cross-adaptation in which the olfactory sensitivity to an underarm odor component is lowered by causing one to continuously smell a substance having an odor which has a chemical structure very similar to that of a causative component of the underarm odor but is weak or not discomfort. Besides, Patent Literature 3 describes a method for evaluating, based on the cross-adaptation, odor similarity between a natural flavor and an imitation flavor imitating the natural flavor. In Patent Literature 3, it is presumed that stronger cross-adaptation is induced as two flavor compositions have odors with more similar odor quality and that the influence of the adaptation is expressed as change in cerebral blood flow, and the similarity of the two flavors is evaluated by using the change in cerebral blood flow as an index.

The lowering of odor sensitivity through the cross-adaptation can be caused not only at the level of olfactory receptors but also through various mechanisms at the level of olfactory neurons, at the level of neural networks and the like. Various hypotheses have been formed as the mechanism of the olfactory cross-adaptation. In one of the hypotheses, the cross-adaptation is regarded to occur in a neuron present in a high-order brain region. Specifically, it is regarded as a mechanism in which the neuron present in the higher-order brain region, where information from peripheral olfactory neurons is integrated to read the nature of an odor, loses its sensitivity so as not to continuously make unnecessary response to odor information remaining without changing. In another hypothesis, the cross-adaptation is regarded to occur at the level of olfactory receptors of peripheral olfactory neurons. Specifically, it is presumed as a mechanism in which an olfactory receptor for a given odorous substance is desensitized as a result of precedently responding to another substance, and hence does not transmit a signal with respect to the odorous substance to which the receptor is exposed afterward. The former hypothesis is difficult to verify because it is still unknown by which high-order brain neural network the odor information is processed. On the other hand, the latter hypothesis is also difficult to verify because of the large number of olfactory receptors, which is said to be 400 or more, and complexity of their combinations in the recognition of odorous substances.

Besides, it is presumed that a substance inducing the cross-adaptation of a given odor is a substance having a very similar chemical structure to a causative substance of the odor or having similar odor quality (Non Patent Literature 3). On the other hand, it is also pointed out that either of these principles does not hold true (Non Patent Literature 4). Non Patent Literature 5 reports that odorous substances accepted by one rat olfactory receptor had similar odor quality, and that the odorous substances induced the cross-adaptation in a human. In general, however, one odorous substance is recognized by a large number of olfactory receptors having different selectivity.

In this manner, the biological mechanism of inducing the cross-adaptation has not been cleared yet, and a method for identifying odorous substances inducing the cross-adaptation has not been established yet. Accordingly, development of a technique to control an odor by artificially and systematically inducing the cross-adaptation has been conventionally very difficult.

(Patent Literature 1) JP-B-5646255
(Patent Literature 2) JP-A-2005-53887
(Patent Literature 3) JP-B-4966790
(Non Patent Literature 1) Shirasu M. et al., Neuron, 81:165-178, 2014
(Non Patent Literature 2) Mainland J. D. et al., Nat. Neurosci., 17(1): 114-20, 2014
(Non Patent Literature 3) Michiaki Kawasaki, Tetsushiro Horiuchi, "Kyukaku to Nioi Busshitsu (Olfactory and Odorous Substances)", p. 71-72, Japan Association on Odor Environment, 1998
(Non Patent Literature 4) Pierce J. D., Chemical senses, 21:223-237, 1996
(Non Patent Literature 5) Chemosensory Perception, 3(3): 149-155, 2010

SUMMARY OF THE INVENTION

The present invention provides a method for selecting a substance inducing cross-adaptation of a target odor, comprising:

(1) searching olfactory receptor polypeptides to identify an olfactory receptor polypeptide responding to a causative substance of the target odor;

(2) adding a test substance to the identified olfactory receptor polypeptide to measure response thereof; and (3) selecting a test substance which activates the response of the olfactory receptor polypeptide as the substance inducing the cross-adaptation of the target odor.

Alternatively, the present invention provides a method for selecting a substance suppressing a target odor, comprising:

(1) searching olfactory receptor polypeptides to identify an olfactory receptor polypeptide responding to a causative substance of the target odor;

(2) adding a test substance to the identified olfactory receptor polypeptide to measure response thereof;

(3) selecting a test substance which activates the response of the olfactory receptor polypeptide as the substance suppressing the target odor.

Alternatively, the present invention provides a method for selecting a substance inducing cross-adaptation of a target odor, comprising:

(1) providing at least one or more types of olfactory receptor polypeptides responding to a causative substance of the target odor;

(2) adding a test substance to the at least one or more types of olfactory receptor polypeptides to measure response thereof; and (3) selecting a test substance which activates the response of any of the at least one or more types of olfactory receptor polypeptides as the substance inducing the cross-adaptation of the target odor.

Alternatively, the present invention provides a method for selecting a substance suppressing a target odor, comprising:

(1) providing at least one or more types of olfactory receptor polypeptides responding to a causative substance of the target odor;

(2) adding a test substance to the at least one or more types of olfactory receptor polypeptides to measure response thereof; and (3) selecting a test substance which activates the response of any of the at least one or more types of olfactory receptor polypeptides as the substance suppressing the target odor.

BRIEF DESCRIPTION OF THE DRAWINGS

FIG. 1 illustrates activity of olfactory receptors to muscone, guaiacol and p-cresol, wherein the abscissa indicates 370 olfactory receptors tested, and the ordinate indicates the relative response intensity of these receptors.

FIG. 2 illustrates activity of an olfactory receptor OR9Q2 to p-cresol, in which Mock indicates activity of a cell not expressing the olfactory receptor, an error bar corresponds to ±SE and n=3 to 4.

FIG. 3 illustrates response of an olfactory receptor OR5AN1-expressing cell to various test substances, in which the abscissa indicates the concentration of each test substance and the ordinate indicates response intensity, Mock indicates response of a cell not expressing the olfactory receptor, an error bar corresponds to ±SE and n=3 to 4.

FIG. 4 illustrates response of an olfactory receptor OR1A1 expressing cell to various test substances, in which the abscissa indicates the concentration of each test substance and the ordinate indicates response intensity, Mock indicates response of a cell not expressing the olfactory receptor, an error bar corresponds to ±SE and n=3.

FIGS. 5A and 5B illustrate response of olfactory receptor OR10G4 (A) or OR9Q2 (B) expressing cells to various test substances, in which the abscissa indicates the concentration of each test substance and the ordinate indicates response intensity, an error bar corresponds to ±SE and n=3, and FIG. 5C illustrates response of an olfactory receptor expressing cells to muscone, in which an error bar corresponds to ±SD and n=2.

FIG. 6A illustrates the cross-adaptation of a muscone odor induced by test substances (n=5 to 7), FIG. 6B illustrates the cross-adaptation of a guaiacol odor induced by test substances (n=7), and FIG. 6C illustrates the cross-adaptation of a p-cresol odor induced by test substances (n=8), in all of which each bar illustrates an average value of estimate results of a sensory test, and an error bar indicates a standard error (SE).

DETAILED DESCRIPTION OF THE INVENTION

Herein, the term "olfactory receptor polypeptide" refers to an olfactory receptor or a polypeptide having a function equivalent to the olfactory receptor, and the term "polypeptide having a function equivalent to the olfactory receptor" refers to a polypeptide which can be expressed on a cell membrane similarly to the olfactory receptor, is activated through binding to an odor molecule, and has, when activated, a function to increase an intracellular cAMP amount by activating adenylate cyclase in conjugation with intracellular Gαs or Gαolf.

Herein, the term "odor cross-adaptation (or olfactory cross-adaptation)" relating to a target odor refers to a phenomenon in which olfactory sensitivity to a causative substance of the target odor is lowered or changed by causing an odor of a substance different from the causative substance of the target odor to be precedently accepted and thereby habituated to the odor. The present inventors have revealed that the "odor cross-adaptation" is a phenomenon based on an olfactory receptor agonism. Specifically, an olfactory receptor for the causative substance of the target odor responds to a causative substance of a different odor priorly to responding to the causative substance of the target odor, and thereafter the response is adapted, and hence, merely low response can be made even if exposed to the causative substance of the target odor afterward, and as a result, the intensity of the target odor recognized by an individual is lowered or altered. Accordingly, for the cross-adaptation of the target odor of the present invention and control of the target odor based on the cross-adaptation, a substance, such as an olfactory receptor agonist, activating response of an olfactory receptor to a causative substance of the target odor can be used.

Herein, a nucleotide sequence or amino acid sequence identity is calculated by the Lipman-Person method (Science, 1985, 227: 1435-41). Specifically, the calculation is carried out by performing analysis using homology analysis (search homology) program of gene information processing software, Genetyx-Win (Ver. 5.1.1; Software Development Co., Ltd.) with the unit size to compare (ktup) set to 2.

Herein, the term "identity of at least 80%" in an amino acid sequence or a nucleotide sequence refers to an identity of 80% or more, preferably 85% or more, more preferably 90% or more, further preferably 95% or more, further more preferably 98% or more and still further preferably 99% or more.

The present invention provides a method for selecting an odorous substance pair inducing the cross-adaptation with response of an olfactory receptor used as an index. Besides, the present invention provides a method for selecting, with activation of an olfactory receptor to a causative substance of a given odor used as an index, a substance suppressing the odor based on the cross-adaptation.

According to the present invention, a substance capable of selectively deodorizing a target odor based on the cross-adaptation can be efficiently selected.

There has been a possibility that cross-adapting substances can be searched for by paying attention to the activity of olfactory receptors involved in recognition of a causative substance of a target odor. Since one odorous substance is recognized by a plurality of olfactory receptors in general, however, such search is complicated, and in addition, it is unknown whether or not a substance thus searched for actually induces the cross-adaptation of the target odor.

The present inventors have successfully verified, for the first time, involvement in the odor cross-adaptation at the level of olfactory receptors by utilizing a simple odor-olfactory receptor model in which high relevance between odor perception and specific olfactory receptor response is suggested, such as between a musk perfume and an olfactory receptor OR5AN1, or between guaiacol (2-methoxyphenol) and an olfactory receptor OR10G4. As a result, the present inventors have found a principle that another substance recognized by an olfactory receptor highly sensitively recognizing a causative substance of a target odor induces the cross-adaptation of the target odor. Besides, the present inventors have confirmed that this principle is universal as a result of experiments further made on another odor-olfactory receptor model (using p-cresol and OR9Q2). Based on these, the present inventors have found that cross-adaptation of various odors can be examined by constructing another odor-olfactory receptor model by screening olfactory receptors with respect to the responsiveness to odorous substances.

Based on the above-described principle, the present invention provides a method for screening or identifying a substance inducing cross-adaptation of a target odor and a substance suppressing the target odor by the cross-adaptation.

Accordingly, the present invention provides a method for selecting a substance inducing cross-adaptation of a target odor, comprising:

(1) searching olfactory receptor polypeptides to identify an olfactory receptor polypeptide responding to a causative substance of the target odor;

(2) adding a test substance to the identified olfactory receptor polypeptide to measure response thereof; and (3) selecting a test substance which activates the response of the olfactory receptor polypeptide as the substance inducing the cross-adaptation of the target odor.

Besides, the present invention provides a method for selecting a substance suppressing a target odor, comprising:

(1) searching olfactory receptor polypeptides to identify an olfactory receptor polypeptide responding to a causative substance of the target odor;

(2) adding a test substance to the identified olfactory receptor polypeptide to measure response thereof;

(3) selecting a test substance which activates the response of the olfactory receptor polypeptide as the substance suppressing the target odor.

Furthermore, the present invention provides a method for selecting a substance inducing cross-adaptation of a target odor, comprising:

(1) providing at least one or more types of olfactory receptor polypeptides responding to a causative substance of the target odor;

(2) adding a test substance to the at least one or more types of olfactory receptor polypeptides to measure response thereof; and (3) selecting a test substance which activates the response of any of the at least one or more types of olfactory receptor polypeptides as the substance inducing the cross-adaptation of the target odor.

Besides, the present invention provides a method for selecting a substance suppressing a target odor, comprising:

(1) providing at least one or more types of olfactory receptor polypeptides responding to a causative substance of the target odor;

(2) adding a test substance to the at least one or more types of olfactory receptor polypeptides to measure response thereof; and (3) selecting a test substance which activates the response of any of the at least one or more types of olfactory receptor polypeptides as the substance suppressing the target odor.

The above-described methods of the present invention are applicable to all olfactory receptor polypeptides involved in odor information transmission and all odors recognized thereby.

The above-described methods of the present invention can be methods performed in vitro or ex vivo. In the methods of the present invention, with respect to a target odor for which cross-adaptation is desired to induce or which is desired to be suppressed, at least one or more olfactory receptor polypeptides having responsiveness to a causative substance of a target odor are first prepared.

The at least one or more olfactory receptor polypeptides responding to the causative substance of the target odor used in the present invention can be obtained by searching a population of olfactory receptor polypeptides to identify one responding to the causative substance of the target odor in the searched population. The "olfactory receptor for the causative substance of the target odor" to be identified need not be all olfactory receptors having accepting ability for the causative substance of the target odor, but may be a receptor playing a significant role in recognition of the target odor, in other words, a receptor capable of responding to the causative substance of the target odor at a comparatively low concentration, or a receptor having comparatively high responsiveness to the causative substance of the odor at a given concentration. Alternatively, the dependency on the concentration of the odor causative substance of the response of a cell expressing a receptor is obtained, and one having a comparatively low concentration effect (EC50) calculated as a result may be identified as the "olfactory receptor for the causative substance of the target odor". Alternatively, if a bond of the odor causative substance to a receptor polypeptide is directly evaluated, the "olfactory receptor for the causative substance of the target odor" to be identified may be a receptor having higher binding capacity such as one having a low dissociation constant.

For example, the olfactory receptor polypeptide having the responsiveness to the causative substance of the target odor can be identified, as described in Example 1 below, by monitoring response of various olfactory receptor polypeptides in accordance with a method described in Reference Examples 1 to 2, and screening an olfactory receptor polypeptide having responsiveness to the causative substance of the target odor.

The olfactory receptor polypeptide used in the methods of the present invention may be an olfactory receptor polypeptide derived from a mammal. Preferable examples of the olfactory receptor polypeptide derived from a mammal include olfactory receptor polypeptides derived from the primates such as a human and a chimpanzee or derived from rodents such as a mouse and a rat, and more preferable examples include 400 or more olfactory receptors of a human and polypeptides having equivalent functions to the receptors. Information on olfactory receptors of a human, a mouse and a rat is available from GenBank [www.ncbi.nlm.nih.gov].

The population of olfactory receptor polypeptides to be searched as described above may be derived from a single mammalian species, or may include olfactory receptor polypeptides derived from two or more different mammalian species. The population of olfactory receptor polypeptides to be searched preferably include either a human, mouse or rat olfactory receptors or polypeptides having an amino acid sequence identity of at least 80% to any of the olfactory receptors and having an equivalent function to the olfactory receptor, and more preferably include either human olfactory receptors or polypeptides having an amino acid sequence identity of at least 80% to any of the olfactory receptors and having an equivalent function to the olfactory receptor.

In the methods of the present invention, the olfactory receptor polypeptide can be used in an arbitrary form as long as the responsiveness to the causative substance of the target odor is not lost. The olfactory receptor polypeptide can be used, for example, in the form of: a tissue or a cell naturally expressing the olfactory receptor polypeptide such as an olfactory receptor or an olfactory cell isolated from a living body, or a culture thereof; an olfactory cell membrane carrying the olfactory receptor polypeptide thereon; a recombinant cell genetically engineered to express the olfactory receptor polypeptide or a culture thereof; a membrane of the recombinant cell having the olfactory receptor polypeptide; or an artificial lipid bilayer membrane having the olfactory receptor polypeptide. All of these forms are embraced in the scope of the olfactory receptor polypeptide used in the present invention.

In a preferable aspect, the olfactory receptor polypeptide can be a cell naturally expressing the olfactory receptor polypeptide such as an olfactory cell of a mammal, a recombinant cell genetically engineered to express the olfactory receptor polypeptide, or a culture of any of these. A preferable example includes a recombinant human cell genetically engineered to express a human olfactory receptor polypeptide.

The recombinant cell can be produced by transforming a cell by using a vector in which a gene encoding the olfactory receptor polypeptide has been incorporated. Alternatively, the olfactory receptor polypeptide can be expressed by directly introducing a transcriptional product of the gene into a cell. Suitably, in order to accelerate the cell membrane expression of the olfactory receptor polypeptide, a gene encoding RTP (receptor-transporting protein) is introduced into a cell together with the gene encoding the olfactory receptor polypeptide. Preferably, a gene encoding RTP1S is introduced into a cell together with the gene encoding the olfactory receptor polypeptide. An example of the RTP1S includes human RTP1S. The human RTP1S refers to a protein registered in GenBank under the accession number GI:50234917.

The type of the target odor is not particularly limited, and embraces all odors including not only generally known offensive or unpleasant odors (such as a body odor, an underarm odor, a mouth odor, a fecal odor, a urine odor, a tobacco odor, a fusty odor, a musty odor, a putrid odor, a garbage odor, a sewage odor, a duct odor and an exhaust gas odor) but also odors derived from food or perfumery substances and odors derived from other substances (such as cosmetics, pharmaceuticals, detergents and daily necessities).

The causative substance of the target odor may be any substance as long as it works on an olfactory receptor to cause the target odor to be perceived. The causative substance may be a natural substance or a substance artificially synthesized by a chemical or biological method, or may be a compound, a composition or a mixture. The causative substance is preferably a volatile substance. Examples of the causative substance include muscone corresponding to a causative substance of a musk odor, guaiacol corresponding to a causative substance of a tobacco odor, p-cresol corresponding to a causative substance of a urine odor, 4-methyl-3-hexenoic acid corresponding to a causative substance of a musty odor, 3-mercapto-3-methylhexanol, 3-hydroxy-3-methylhexanoic acid and 3-methyl-2-hexenoic acid corresponding to causative substances of an underarm odor, diosmin and 2-methylisoborneol corresponding to causative substances of a fusty odor, skatole and indole corresponding to causative substance of a fecal odor or a mouth odor, nonanoic acid, hexanoic acid and isovaleric acid corresponding to causative substances of a body odor, volatile sulfur compounds corresponding causative substances of offensive odors generated from a garbage, a sewage or a drainage, and butyl acrylate, a pyrazine derivative, furaneol and sotolon.

The causative substance of the target odor is added to the olfactory receptor polypeptide, and the response to the causative substance is measured. The measurement may be performed by any arbitrary method known, in the art, as a method for measuring response of an olfactory receptor, such as measurement of an intracellular cAMP amount. For example, it is known that an olfactory receptor, having been activated by an odor molecule, activates adenylate cyclase in conjugation with intracellular Gαs to increase an intracellular cAMP amount. Accordingly, when the intracellular cAMP amount obtained after the addition of the causative substance is used as an index, the response of the olfactory receptor polypeptide to the causative substance can be measured. Examples of a method for measuring the cAMP amount include the ELISA method and reporter gene assay. Another example of the method for measuring the response of an olfactory receptor polypeptide includes a calcium imaging method. Still another example includes measurement by an electrophysiological method. In electrophysiological measurement, for example, a cell (such as a *xenopus* oocyte) in which an olfactory receptor polypeptide is co-expressed with another ion channel is produced, and the activity of the ion channel on this cell is measured by a patch-clamp method, a two-electrode voltage clamp method or the like, and thus, the response of the olfactory receptor polypeptide is measured.

Subsequently, on the basis of the measured response, an olfactory receptor polypeptide responding to the causative substance of the target odor is identified. The evaluation of the responsiveness can be performed by comparing the response of the olfactory receptor polypeptide to which the causative substance has been added (a test group) with that of a control group. Examples of the control group include the olfactory receptor polypeptide to which the causative substance in a different concentration has been added, the olfactory receptor polypeptide to which the causative substance has not been added, the olfactory receptor polypeptide to which a control substance has been added, the olfactory receptor polypeptide before adding the causative substance, and a cell in which the olfactory receptor polypeptide has not been expressed. Another example of the control group includes another olfactory receptor polypeptide having no responsiveness or low responsiveness to the causative substance.

When the response of the test group is increased as compared with that of the control group, the olfactory receptor polypeptide is identified to respond to the causative substance of the target odor. For example, when the response of the olfactory receptor polypeptide of the test group is increased, as compared with that of the control group, preferably by 200% or more, more preferably by 300% or more, and further preferably by 400% or more, the olfactory receptor polypeptide is identified to respond to the causative substance of the target odor. Alternatively, when the response of the olfactory receptor polypeptide of the test group is increased statistically significantly as compared with that of the control group, the olfactory receptor polypeptide is identified to respond to the causative substance of the target odor.

If necessary, the response may be measured in a similar manner with the causative substance of the target odor added in a different concentration to the identified olfactory receptor polypeptide. If the response is increased dependently on the concentration of the causative substance, it can be confirmed that the olfactory receptor polypeptide has responsiveness to the causative substance of the target odor.

If a plurality of olfactory receptor polypeptides having responsiveness to the causative substance of the target odor are found and their response intensities are different from one another, one of the olfactory receptor polypeptides having comparatively high responsiveness to the causative substance can be further selected from these. For example, one, two, three or more olfactory receptor polypeptides having higher responsiveness to the causative substance of the target odor can be selected, and one having the highest responsiveness can be further selected. Alternatively, an olfactory receptor polypeptide having the lowest responsiveness to the causative substance of the target odor may be eliminated from selection, or two or more having a lower responsiveness may be further eliminated from the selection. Suitably, the one or more olfactory receptor polypeptides to be "selected" have responsiveness of 200% or more, preferably 300% or more, and more preferably 400% or more as compared with each of the olfactory receptor polypeptides to be "eliminated" from the selection. Alternatively, the response sensitivity of the olfactory receptor polypeptide to the causative substance of the target odor can be evaluated using an index of EC50, a response threshold value or the like, so as to select an olfactory receptor polypeptide having high sensitivity. Besides, based on the evaluation of the responsiveness and the response sensitivity, an olfactory receptor polypeptide having high sensitivity and high responsiveness can be selected.

When expressed on a cultured cell or the like, an olfactory receptor polypeptide shows different basal activity depending on the type thereof. Therefore, when the response is compared among olfactory receptor polypeptides, a response value of each olfactory receptor polypeptide is normalized, so that the comparison among the olfactory receptor polypeptides can be preferably performed based on the thus obtained normalized values. Examples of a normalization method include a method in which in a cell expressing one olfactory receptor, a relative value of a signal obtained in response to odor stimulation is obtained on the assumption that a signal value obtained without the odor stimulation is 1, and a method in which in a cell expressing one olfactory receptor, a signal value obtained without odor stimulation is subtracted from a signal value obtained in response to the odor stimulation.

In this manner, an olfactory receptor polypeptide having the responsiveness to the causative substance of the target odor can be identified. Thus, at least one olfactory receptor polypeptide having the responsiveness to the causative substance of the target odor is prepared.

An example of the at least one or more olfactory receptor polypeptides provided in the methods of the present invention includes at least one selected from the group consisting of a human, mouse or rat olfactory receptor having responsiveness to the causative substance of the target odor, and a polypeptide having an amino acid sequence identity of at least 80% to the olfactory receptor and having responsiveness to the causative substance of the target odor. A more preferable example includes at least one selected from the group consisting of a human olfactory receptor having responsiveness to the causative substance of the target odor, and a polypeptide having an amino acid sequence identity of at least 80% to the human olfactory receptor and having responsiveness to the causative substance of the target odor. A still more preferable example includes at least one selected from the group consisting of an olfactory receptor having highest responsiveness in a group of human olfactory receptors having responsiveness to the causative substance of the target odor, and a polypeptide having an amino acid sequence identity of at least 80% to the olfactory receptor and having responsiveness to the causative substance of the target odor. A still more preferable example includes at least one selected from the group consisting of an olfactory receptor having highest sensitivity and highest responsiveness in a group of human olfactory receptors having responsiveness to the causative substance of the target odor, and a polypeptide having an amino acid sequence identity of at least 80% to the olfactory receptor and having responsiveness to the causative substance of the target odor.

The olfactory receptor polypeptide(s) provided in the methods of the present invention may be at least one having the responsiveness to the causative substance of the target odor, and may be a combination of any two or more of these.

If the target odor is, for example, musk fragrance in the methods of the present invention, the odor causative substance is a musk perfume, and an olfactory receptor polypeptide to be used is at least one selected from the group consisting of OR5AN1 (SEQ ID NO: 2) and a polypeptide having an amino acid sequence identity of at least 80% to the amino acid sequence as set forth in SEQ ID NO: 2 and having responsiveness to the musk perfume (see FIG. 1).

Alternatively, if the target odor is, for example, an odor of guaiacol (2-methoxyphenol) in the methods of the present invention, the odor causative substance is guaiacol, and an olfactory receptor polypeptide to be used is at least one selected from the group consisting of OR10G4 (SEQ ID NO: 4) and a polypeptide having an amino acid sequence identity of at least 80% to the amino acid sequence as set forth in SEQ ID NO: 4 and having responsiveness to guaiacol (see FIG. 1).

The guaiacol is known as a principal causative substance of a tobacco odor (JP-A-2006-321943). Accordingly, in one embodiment of the methods of the present invention, the target odor is a tobacco odor, and an olfactory receptor polypeptide to be used is at least one selected from the group consisting of the OR10G4 (SEQ ID NO: 4), that is, a guaiacol receptor, and a polypeptide having an amino acid sequence identity of at least 80% to the amino acid sequence as set forth in SEQ ID NO: 4 and having responsiveness to a tobacco odor causative substance, preferably the guaiacol.

In one embodiment of the methods of the present invention, the target odor is a urine odor. JP-A-2009-132770 describes that a component having the highest contribution to a urine odor generated from scattered and dried urine or a diaper left after use is p-cresol, and that a urine odor can be reproduced by a composition containing p-cresol and another phenol compound having 6 to 10 carbon atoms. International Publication No. WO 2009/037861 describes that when β-glucuronidase produced by a bacteria works on urine, p-cresol or another component is increased in the urine, resulting in remarkably increasing the intensity of the urine odor. Besides, the present applicant has found that a substance inhibiting responsiveness of an olfactory receptor to p-cresol can suppress a urine odor, and has filed a patent application (JP Application No. 2015-060636). Accordingly, examples of a "urine odor causative substance" of the present invention include β-glucuronidase treated urine or an extract thereof, and p-cresol. Examples of the β-glucuronidase treated urine include urine having been treated by adding β-glucuronidase thereto, and urine affected by β-glucuronidase produced by a bacteria present in the urine. Such a treated urine or an extract thereof comprises p-cresol.

As an olfactory receptor recognizing p-cresol corresponding to the urine odor causative substance, OR9Q2 has been found (see FIGS. 1 and 2). The OR9Q2 is a polypeptide registered in GenBank under the accession number GI:284413710 and consisting of an amino acid sequence as set forth in SEQ ID NO: 6. Accordingly, if the target odor is a urine odor in the methods of the present invention, an olfactory receptor polypeptide to be used is preferably at least one selected from the group consisting of the OR9Q2 (SEQ ID NO: 6) and a polypeptide having an amino acid sequence identity of at least 80% to the amino acid sequence as set forth in SEQ ID NO: 6 and having responsiveness to a urine odor causative substance, preferably p-cresol.

Subsequently, in the methods of the present invention, a test substance is added to the olfactory receptor polypeptide having the responsiveness to the causative substance of the target odor.

The test substance used in the methods of the present invention is not particularly limited as long as it is a substance desired to be used as a substance inducing the cross-adaptation of the target odor or as a substance suppressing the target odor. The test substance may be a natural substance or a substance artificially synthesized by a chemical or biological method or the like, or may be a compound, a composition or a mixture. It is noted that the test substance is a substance different from the causative substance of the target odor. The test substance is preferably a volatile substance having a different odor from the target odor. Besides, the test substance is preferably a perfume having a different odor from the target odor.

Subsequently, the response of the olfactory receptor polypeptide to the test substance is measured. The measurement may be performed in accordance with the method described above with respect to the measurement of the response of an olfactory receptor polypeptide to the causative substance of the target odor.

Next, on the basis of the measured response of the olfactory receptor polypeptide, the receptor activating effect of the test substance is evaluated to identify a test substance inducing the cross-adaptation of the target odor. The evaluation of the effect of the test substance can be performed by comparing the response of the olfactory receptor to which the test substance has been added (the test group) with that of a control group. Examples of the control group include the olfactory receptor polypeptide to which the test substance in a different concentration has been added, the olfactory receptor polypeptide to which the test substance has not been added, the olfactory receptor polypeptide to which a control substance has been added, the olfactory receptor polypeptide before adding the test substance, and a cell in which the olfactory receptor polypeptide has not been expressed. Another example of the control group includes another olfactory receptor polypeptide having no responsiveness or low responsiveness to the test substance.

If the response of the test group is increased as compared with that of the control group, the test substance can be evaluated to be a substance activating the response of the olfactory receptor polypeptide. For example, the effect of a test substance on the response of an olfactory receptor polypeptide can be evaluated by comparing the response of the olfactory receptor polypeptide between a group in which the test substance has been added and a group in which it has not been added, between a group in which the test substance has been added and a group in which a control substance has been added, between before and after adding the test substance, or between a group in which the olfactory receptor polypeptide has been expressed and a group in which it has not been expressed. If the response of the olfactory receptor polypeptide has been induced by the addition of a test substance, the test substance is evaluated to be a substance activating the response of the olfactory receptor polypeptide to the causative substance of the target odor.

For example, when the response of the olfactory receptor polypeptide of the group in which the test substance has been added is increased, as compared with that of the control group, preferably by 200% or more, more preferably by 300% or more, and further preferably by 400% or more, the test substance is evaluated to be a substance activating the response of the olfactory receptor polypeptide. Alternatively, when the response of the olfactory receptor polypeptide of the group in which the test substance has been added is increased statistically significantly as compared with that of the control group, the test substance can be evaluated to be a substance activating the response of the olfactory receptor polypeptide.

The test substance activating the response of the olfactory receptor polypeptide to the causative substance of the target odor obtained as described above is selected as a substance inducing the cross-adaptation of the target odor. Specifically, the olfactory receptor recognizing the target odor is activated in the presence of the test substance, and is subsequently lowered in the responsiveness due to the adaptation, and hence, loses the responsiveness to the causative substance of the target odor added afterward. As a result, the cross-adaptation of the target odor is induced by the test substance.

Alternatively, the test substance activating the response of the olfactory receptor polypeptide to the causative substance of the target odor obtained as described above is selected as a substance suppressing the target odor. Specifically, the test substance is a substance capable of suppressing the target odor by inducing the cross-adaptation of the target odor.

In the methods of the present invention, the test substance selected as described above may be subjected to a sensory test, if necessary, to further estimate level of cross-adaptation or extent of target odor suppression thereof. The sensory test can be performed in accordance with an estimation procedure for a deodorant usually employed in the art, and considering that the test substance is a cross-adaptation inducer substance, the order of applying the test substance and the causative substance of the target odor to an estimator is preferably adjusted. For example, in the sensory test of the present invention, an estimator has been precedently adapted to an odor of a candidate test substance selected as described above by smelling the odor. Subsequently, the estimator smells the target odor to estimate the intensity of the odor. The thus obtained estimation result is compared with the intensity of the target odor perceived without the adaptation to the test substance. A test substance estimated, as a result of the sensory test, to lower the intensity of the target odor is selected as a substance inducing the cross-adaptation of the target odor, or a substance suppressing the target odor.

A substance selected by the methods of the present invention is a substance capable of suppressing the target odor on the basis of the cross-adaptation. One embodiment of usage of the substance suppressing the target odor obtained by the methods of the present invention is as follows: First, a subject desired to suppress the target odor is caused to smell the substance suppressing the target odor before exposing the subject to the target odor. Alternatively, the substance suppressing the target odor is applied to the subject so that an odor of the substance can be stronger than the target odor. As a result, since olfactory sensitivity to the target odor of the subject is thus lowered, he/she perceives that the target odor is weak or does not perceive the target odor even when exposed to the target odor. Examples of the application of the substance suppressing the target odor obtained by the present invention include, but are not limited to: placement of the substance in front of or in a toilet; a method in which a person in charge of excretion care in a hospital ward or aged care facilities is caused to carry the substance with him/her or exposed to the substance before the care; a paper diaper or a sanitary napkin containing the substance; clothes, cloth products and fabrics such as underwear, underclothes and linens containing the substance; laundry detergents and softeners containing the substance; cosmetics, detergents, external preparations such as deodorants, pharmaceuticals and food containing the substance; and application to a manufacturing line for products having the target odor or an environment where the target odor is generated.

As exemplified embodiments of the present invention, the following substance, production method, use and methods are herein disclosed. It is noted that the present invention is not limited to these embodiments.

<1> A method for selecting a substance inducing cross-adaptation of a target odor, comprising:
(1) searching olfactory receptor polypeptides to identify an olfactory receptor polypeptide responding to a causative substance of the target odor;
(2) adding a test substance to the identified olfactory receptor polypeptide to measure response thereof; and
(3) selecting a test substance which actives the response of the olfactory receptor polypeptide as the substance inducing the cross-adaptation of the target odo.

<2> A method for selecting a substance suppressing a target odor, comprising:
(1) searching olfactory receptor polypeptides to identify an olfactory receptor polypeptide responding to a causative substance of the target odor;
(2) adding a test substance to the identified olfactory receptor polypeptide to measure response thereof; and
(3) selecting a test substance which activates the response of the olfactory receptor polypeptide as the substance suppressing the target odor.

<3> The method according to <1> or <2>, in which the olfactory receptor polypeptides searched in (1) above are preferably a population of olfactory receptor polypeptides comprising any one of human, mouse and rat olfactory receptors, and polypeptides having an amino acid sequence identity of at least 80% to the olfactory receptors and having an equivalent function to the olfactory receptors.

<4> A method for selecting a substance inducing cross-adaptation of a target odor, comprising:
(1) providing at least one or more olfactory receptor polypeptides responding to a causative substance of the target odor;
(2) adding a test substance to the at least one or more olfactory receptor polypeptides to measure response thereof; and
(3) selecting a test substance which activates the response of any of the at least one or more olfactory receptor polypeptides as the substance inducing the cross-adaptation of the target odor.

<5> A method for selecting a substance suppressing a target odor, comprising:
(1) providing at least one or more types of olfactory receptor polypeptides responding to a causative substance of the target odor;
(2) adding a test substance to the at least one or more types of olfactory receptor polypeptides to measure response thereof; and
(3) selecting a test substance which activates the response of any of the at least one or more types of olfactory receptor polypeptides as the substance suppressing the target odor.

<6> The method according to <4> or <5>, in which the at least one or more types of olfactory receptor polypeptides are preferably at least one selected from the group consisting of the following:

a rat or mouse olfactory receptor;
a human olfactory receptor; and
a polypeptide having an amino acid sequence identity of 80% or more, preferably 85% or more, more preferably 90% or more, further preferably 95% or more, still further preferably 98% or more, and still further preferably 99% or more to the rat, mouse or human olfactory receptor, and having responsiveness to the causative substance of the target odor.

<7> The method according to any one of <1> to <6>, in which the olfactory receptor polypeptide is preferably expressed on a recombinant cell genetically engineered to express the olfactory receptor polypeptide.

<8> The method according to any one of <1> to <7>, wherein the response of the olfactory receptor polypeptide is preferably measured by intracellular cAMP amount measurement by ELISA or reporter gene assay, or by calcium imaging or an electrophysiological method.

<9> The method according to any one of <1> to <8>, further comprising (4) selecting the substance inducing the cross-adaptation to the target odor or the substance suppressing the target odor from substances selected in (3) above by a sensory test.

<10> The method according to any one of <1> to <9>, in which the target odor is preferably a tobacco odor or a urine odor.

<11> The method according to any one of <4> to <9>, in which the target odor is preferably a tobacco odor, and the at least one or more olfactory receptor polypeptides are preferably at least one selected from the group consisting of:
a polypeptide consisting of an amino acid sequence as set forth in SEQ ID NO: 4; and
a polypeptide having an amino acid sequence identity of 80% or more, preferably 85% or more, more preferably 90% or more, further preferably 95% or more, still further preferably 98% or more, and still further preferably 99% or more to the amino acid sequence as set forth in SEQ ID NO: 4, and having responsiveness to a tobacco odor causative substance.

<12> The method according to any one of <4> to <9>, in which the target odor is preferably a urine odor, and the at least one or more olfactory receptor polypeptides are preferably at least one selected from the group consisting of:
a polypeptide consisting of an amino acid sequence as set forth in SEQ ID NO: 6; and
a polypeptide having an amino acid sequence identity of 80% or more, preferably 85% or more, more preferably 90% or more, further preferably 95% or more, still further preferably 98% or more, and still further preferably 99% or more to the amino acid sequence as set forth in SEQ ID NO: 6, and having responsiveness to a urine odor causative substance.

<13> The method according to any one of <1> to <12>, in which the test substance is preferably different from the causative substance of the target odor.

<14> The method according to any one of <1> to <13>, further comprising selecting an olfactory receptor polypeptide having high responsiveness to the causative substance from at least one or more olfactory receptor polypeptides having the responsiveness to the causative substance of the target odor, and identifying the selected olfactory receptor polypeptide as an olfactory receptor polypeptide responding to the causative substance of the target odor.

EXAMPLES

The present invention will now be more specifically described with reference to Examples.

Reference Example 1 Preparation of Human Olfactory Receptor Expressing Cell

1) Cloning of Human Olfactory Receptor Gene

On the basis of sequence information registered in GenBank, genes respectively encoding 370 human olfactory receptors shown in Tables 1-1 and 1-2 and genes respectively encoding the human olfactory receptors OR5AN1, OR10G4 and OR9Q2 (respectively set forth in SEQ ID NOS: 1, 3 and 5) were cloned. Each of the genes was cloned by the PCR using human genomic DNA female (G1521: Promega) as a template. Each gene amplified by the PCR was incorporated into a pENTR vector (Invitrogen) in accordance with the instruction, and was recombined to NotI and AscI sites produced downstream from a Flag-Rho tag sequence on a pME18S vector by using NotI and AscI sites present on the pENTR vector.

TABLE 1-1

List of Olfactory Receptors used in Examples (Names according to GenBank [www.ncbi.nlm.nih.gov/genbank/])

| | | | | | | | |
|---|---|---|---|---|---|---|---|
| OR1A1 | OR2D2 | OR4A16 | OR4X2 | OR5T2 | OR8B4 | OR10H3 | OR51F1 |
| OR1A2 | OR2D3 | OR4A47 | OR5A1 | OR5T3 | OR8B8 | OR10H4 | OR51F2 |
| OR1B1 | OR2F1 | OR4B1 | OR5A2 | OR5U1 | OR8B12 | OR10H5 | OR51G1 |
| OR1C1 | OR2F2 | OR4C3 | OR5AC2 | OR5V1 | OR8D1 | OR10J1 | OR51G2 |
| OR1D2 | OR2G2 | OR4C6 | OR5AK2 | OR5W2 | OR8D2 | OR10J3 | OR51I1 |
| OR1D4 | OR2G3 | OR4C11 | OR5AN1 | OR6A2 | OR8D4 | OR10J5 | OR51I2 |
| OR1D5 | OR2G6 | OR4C12 | OR5AP2 | OR6B1 | OR8G1 | OR10K1 | OR51L1 |
| OR1E1 | OR2H1 | OR4C13 | OR5AR1 | OR6B2 | OR8G2 | OR10K2 | OR51M1 |
| OR1E2 | OR2H2 | OR4C15 | OR5AS1 | OR6B3 | OR8G5 | OR10P1 | OR51Q1 |
| OR1F1 | OR2J2 | OR4C16 | OR5AT1 | OR6C1 | OR8H1 | OR10Q1 | OR51S1 |
| OR1G1 | OR2J3 | OR4C45 | OR5AU1 | OR6C2 | OR8H2 | OR10R2 | OR51T1 |
| OR1I1 | OR2K2 | OR4C46 | OR5B2 | OR6C3 | OR8H3 | OR10S1 | OR51V1 |
| OR1J1 | OR2L2 | OR4D1 | OR5B3 | OR6C4 | OR8I2 | OR10T2 | OR52A1 |
| OR1J2 | OR2L3 | OR4D2 | OR5B12 | OR6C6 | OR8J1 | OR10V1 | OR52A4 |
| OR1J4 | OR2L8 | OR4D5 | OR5B17 | OR6C65 | OR8J3 | OR10W1 | OR52A5 |
| OR1K1 | OR2L13 | OR4D6 | OR5B21 | OR6C68 | OR8K1 | OR10X1 | OR52B2 |
| OR1L1 | OR2M2 | OR4D9 | OR5BF1 | OR6C70 | OR8K3 | OR10Z1 | OR52B4 |
| OR1L3 | OR2M3 | OR4D10 | OR5BU1 | OR6C74 | OR8K5 | OR11A1 | OR52B6 |
| OR1L4 | OR2M4 | OR4D11 | OR5C1 | OR6C75 | OR8U1 | OR11G2 | OR52D1 |
| OR1L6 | OR2M5 | OR4E2 | OR5D13 | OR6C76 | OR8U8 | OR11H1 | OR52E2 |
| OR1L8 | OR2M7 | OR4F3 | OR5D14 | OR6F1 | OR8U9 | OR11H4 | OR52E4 |
| OR1M1 | OR2S2 | OR4F4 | OR5D16 | OR6K2 | OR9A2 | OR11H6 | OR52E6 |
| OR1N1 | OR2T1 | OR4F5 | OR5D18 | OR6K3 | OR9A4 | OR11L1 | OR52E8 |
| OR1N2 | OR2T2 | OR4F6 | OR5F1 | OR6K6 | OR9G1 | OR12D2 | OR52H1 |

TABLE 1-2

List of Olfactory Receptors used in Examples (Names according to GenBank [www.ncbi.nlm.nih.gov/genbank/])

| | | | | | | | |
|---|---|---|---|---|---|---|---|
| OR1Q1 | OR2T3 | OR4F15 | OR5H1 | OR6M1 | OR9G4 | OR12D3 | OR52I1 |
| OR1S1 | OR2T4 | OR4F16 | OR5H2 | OR6N1 | OR9G9 | OR13A1 | OR52I2 |
| OR1S2 | OR2T5 | OR4F17 | OR5H6 | OR6N2 | OR9I1 | OR13C2 | OR52J3 |
| OR2A1 | OR2T6 | OR4F21 | OR5H14 | OR6Q1 | OR9K2 | OR13C3 | OR52K1 |
| OR2A2 | OR2T8 | OR4F29 | OR5H15 | OR6S1 | OR9Q1 | OR13C4 | OR52K2 |
| OR2A4 | OR2T10 | OR4K1 | OR5I1 | OR6T1 | OR9Q2 | OR13C5 | OR52L1 |
| OR2A5 | OR2T11 | OR4K2 | OR5J2 | OR6V1 | OR10A2 | OR13C8 | OR52M1 |
| OR2A7 | OR2T12 | OR4K5 | OR5K1 | OR6X1 | OR10A3 | OR13C9 | OR52N1 |
| OR2A12 | OR2T27 | OR4K13 | OR5K2 | OR6Y1 | OR10A4 | OR13D1 | OR52N2 |
| OR2A14 | OR2T29 | OR4K14 | OR5K3 | OR7A5 | OR10A5 | OR13F1 | OR52N5 |
| OR2A25 | OR2T33 | OR4K15 | OR5K4 | OR7A10 | OR10A6 | OR13G1 | OR52R1 |
| OR2A42 | OR2T34 | OR4K17 | OR5L1 | OR7A17 | OR10A7 | OR13H1 | OR52W1 |
| OR2AE1 | OR2V2 | OR4L1 | OR5L2 | OR7C1 | OR10AD1 | OR13J1 | OR56A1 |
| OR2AG1 | OR2W1 | OR4M1 | OR5M1 | OR7C2 | OR10AG1 | OR51A2 | OR56A3 |
| OR2AG2 | OR2W3 | OR4M2 | OR5M3 | OR7D2 | OR10C1 | OR51A4 | OR56A4 |
| OR2AK2 | OR2W5 | OR4N2 | OR5M8 | OR7D4 | OR10G2 | OR51A7 | OR56B1 |
| OR2AT4 | OR2Z1 | OR4N4 | OR5M9 | OR7E24 | OR10G3 | OR51B2 | OR56B4 |
| OR2B11 | OR3A1 | OR4N5 | OR5M10 | OR7G1 | OR10G4 | OR51B4 | |
| OR2B2 | OR3A2 | OR4P4 | OR5M11 | OR7G2 | OR10G7 | OR51B5 | |
| OR2B3 | OR3A3 | OR4Q3 | OR5P2 | OR7G3 | OR10G8 | OR51B6 | |
| OR2B6 | OR3A4 | OR4S1 | OR5P3 | OR8A1 | OR10G9 | OR51D1 | |
| OR2C1 | OR4A5 | OR4S2 | OR5R1 | OR8B2 | OR10H1 | OR51E1 | |
| OR2C3 | OR4A15 | OR4X1 | OR5T1 | OR8B3 | OR10H2 | OR51E2 | |

2) Production of pME18S-Human RTP1S Vector

A gene encoding human RTP1S was incorporated into the EcoRI and XhoI sites of the pME18S vector.

3) Production of Olfactory Receptor Expressing Cell

In 1) of Example 1, HEK293 cells on which the 370 human olfactory receptors were respectively expressed were produced. A reaction solution having a composition shown in Table 2 was prepared and allowed to stand still in a clean bench for 15 minutes, and the resultant was added by 4.4 μL per well in a 384-well plate (BioCoat). Subsequently, the HEK293 cells ($20 \times 10^4$ cells/cm$^2$) were seeded by 40 μL per well, and the resultant was cultured for 24 hours in an incubator kept at 37° C. and 5% $CO_2$.

TABLE 2

| | |
|---|---|
| DMEM (4.5 g/l Glucose) with L-Gln and Sodium Pyruvate, liquid (Nacalai Tesque, Inc.) | 2.2 μL |
| TE (pH 8.0: 10 mM Tris-HCl, 1 mM EDTA, Nippon Gene Co., Ltd.) | 2.2 μL |
| Human Olfactory Receptor Gene (incorporated into pME18S vector having Flag-Rho tag added at N-terminal) | 0.029 μg |
| pGL4.29 (fluc2P-CRE-hygro, Promega) | 0.022 μg |
| pGL4.75 (hRluc-CMV, Promega) | 0.0012 μg |
| pME18S human RTP1S vector | 0.012 μg |
| lipofectamine 2000 (Invitrogen) or PEI-MAX (Polyscience) | 0.16 μL |

In 2) of Example 1 and Examples 2 and 3, HEK293 cells in which the human olfactory receptor OR5AN1, OR10G4, OR9Q2 or OR1A1 was expressed were produced. A reaction solution having a composition shown in Table 3 was prepared and allowed to stand still in a clean bench for 15 minutes, and the resultant was added by 10 μL per well in a 96-well plate (BioCoat). Subsequently, the HEK293 cells ($3 \times 10^5$ cells/cm$^2$) were seeded by 90 μL per well, and the resultant was cultured for 24 hours in an incubator kept at 37° C. and 5% $CO_2$. Cells obtained under conditions for not expressing the olfactory receptor (Mock) were also prepared to be used as a control, and were used similarly in an experiment.

TABLE 3

| | |
|---|---|
| DMEM ((4.5 g/l Glucose) with L-Gln and Sodium Pyruvate, liquid, Nacalai Tescqhe, Inc.) | 10 μL |
| Human Olfactory Receptor Gene (any of OR5AN1, OR10G4, OR9Q2 and OR1A1) (incorporated into pME18S vector having Flag-Rho tag added at N-terminal) | 0.075 μg |
| pGL4.29 (fluc2P-CRE-hygro, Promega) | 0.03 μg |
| pGL4.75 (hRluc-CMV, Promega) | 0.03 μg |
| pME18S human RTP1S vector | 0.03 μg |
| lipofectamine 2000 (Invitrogen) or PEI-MAX (Polyscience) | 0.41 μL |

Reference Example 2 Luciferase Assay

The olfactory receptor expressed on the HEK293 cells increases the intracellular cAMP amount by activating adenylate cyclase in conjugation with intracellular Gαs. In the measurement of odor response in this study, luciferase reporter gene assay for monitoring the increase of the intracellular cAMP amount as a luminescence value derived from a firefly luciferase gene (fluc2P-CRE-hygro) was employed. Besides, a fused *Renilla* luciferase (hRluc-CMV) gene was simultaneously transferred downstream of the CMV promoter, so as to be used as an internal standard for correcting the gene transfer efficiency or an error in the number of cells. For measuring the activity of the luciferase, Dual-Glo(™) Luciferase Assay System (Promega) was used, and the measurement was performed in accordance with the operation instruction of the product. Under each of various stimulation conditions, a value fLuc/hRluc obtained by dividing a firefly luciferase-derived luminescence value by a *Renilla* luciferase-derived luminescence value was calculated. A value obtained by dividing a value fLuc/hRluc induced by stimulation with an odorous substance by a value fLuc/hRluc of a cell not stimulated with the odorous substance was obtained as fold increase, which was used as an index of the response intensity. A dose-response curve was analyzed using Graph Pad Prism.

Reference Example 3 Odorous Substances

The following substances were used as odorous substances:

Muscone ((R)-3-methyl-1-cyclopentadecanone; MP Biomedical)

Musk xylol (1-tert-butyl-3,5-dimethyl-2,4,6-trinitrobenzene; Tokyo Chemical Industry Co., Ltd.)

Muscenone delta (3-methyl-5-cyclopentadecen-1-one; FIRMENICH)

Globanone (cyclohexadec-8-en-1-one; SYMRISE)

Exaltolide (R) (16-oxacyclohexadecan-1-one; FIRMENICH)

Ambrettolide (17-oxacycloheptadec-6-en-1-one; Sigma-Aldrich)

Phenyl ethyl alcohol (PEA) (2-phenylethanol; Sigma-Aldrich)

Lyral (R) (4-(4-hydroxy-4-methyl-pentyl)-cyclohex-3-enecarbaldehyde; Takasago International Corporation or IFF)

Cis-3-hexenol (Sigma-Aldrich)

Guaiacol (2-methoxyphenol; Tokyo Chemical Industry Co., Ltd.)

Ethyl vanillin (3-ethoxy-4-hydroxybenzaldehyde; Sigma-Aldrich)

p-Cresol p-Cresyl acetate ((4-methylphenyl)acetate; Tokyo Chemical Industry Co., Ltd.)

p-Cresyl isobutyrate (p-tolyl isobutyrate or (4-methylphenyl)2-methylpropanoate; Tokyo Chemical Industry Co., Ltd.)

p-Methyl quinoline (6-methyl quinoline; Sigma-Aldrich)

Example 1

Response of Olfactory Receptor to Odorous Substance

1) Identification of Olfactory Receptor Responding to Odorous Substance

The medium was removed from each of the cultures of the olfactory receptor expressing cells produced according to Reference Example 1, and an odorous substance (muscone, guaiacol or p-cresol) was added thereto. A DMEM medium (Nacalai) containing muscone or guaiacol was added to a 384-well plate containing the culture by 30 µL per well (to a final concentration of muscone of 100 µM and of guaiacol of 1 mM). Alternatively, a CD293 medium (Invitrogen) containing p-cresol was added to a 96-well plate containing the culture by 75 µL per well (to a final concentration of 1 mM). The resultant cells were cultured in a $CO_2$ incubator for 2.5 to 3 hours to sufficiently express the luciferase gene in the cells, and the response intensity (fold increase) of each olfactory receptor to each odorous substance was measured by the luciferase assay by the method described in Reference Example 2.

The results are illustrated in FIG. 1. The ordinate indicates the relative intensity of the response of the respective receptor expressing cells to the odor stimulation assuming that the response intensity obtained without the odor stimulation was 1. As receptors having the highest responsiveness to muscone, guaiacol and p-cresol, the OR5AN1, the OR10G4 and the OR9Q2 were respectively identified.

2) Dependency on Odorous Substance Concentration of Olfactory Receptor Response

In accordance with the method described in Reference Examples 1 and 2, the response of the OR9Q2 to p-cresol at different concentrations were measured. As a result, the OR9Q2 showed response to p-cresol dependently on the concentration, and was confirmed to be a p-cresol receptor (FIG. 2).

Example 2

Effect of Odorous Substance on Olfactory Receptor

1) Measurement of Response of Olfactory Receptor

The medium was removed from each culture of the olfactory receptor expressing cells produced in accordance with Reference Example 1, and 75 µL of a solution containing an odorous substance prepared in a DMEM medium (Nacalai Tesque, Inc.) to be 0.3 µM to 100 µM was added thereto. The resultant cells were cultured in a $CO_2$ incubator for 3 to 4 hours to sufficiently express the luciferase gene in the cells, and the luciferase assay was performed by the method described in Reference Example 2 to measure the response intensity (fold increase) of the olfactory receptor to the odorous substance.

2) Results

The OR5AN1 is an olfactory receptor responding to a musk perfume. Nine substances were applied to the OR5AN1, and as a result, not only muscone but also Musk xylol, Muscenone delta, Globanone and Exaltolide (R) were found to be substances activating the response. The OR5AN1 responded to these substances concentration-dependently (FIG. 3). Such response was not found in the cells (Mock) in which the OR5AN1 was not expressed, and hence depends on the OR5AN1. On the other hand, Ambrettolide, phenyl ethyl alcohol (PEA), Lyral (R) and Cis-3-hexenol did not induce the response of the OR5AN1.

On the other hand, the OR1A1 (FIG. 1) having weaker responsiveness to muscone than the OR5AN1 was activated also by PEA and Cis-3-hexenol (FIG. 4).

It was confirmed that the OR10G4 had responsiveness to guaiacol and ethyl vanillin (FIG. 5A).

The OR9Q2 was found to have responsiveness to p-cresol, that is, a urine odor causative substance, as illustrated in FIG. 2, and was also found to have responsiveness to p-cresyl acetate, p-cresyl isobutyrate and p-methyl quinoline (FIG. 5B). On the other hand, it was found that both the OR10G4 and the OR9Q2 do not have responsiveness to muscone (FIG. 5C).

Example 3

Sensory Estimation of Cross-Adaptation Effect Induced by Odorous Substance

1) Method

The cross-adaptation effect induced by the odorous substance evaluated in Example 2 was estimated by a sensory test. A glass bottle (No. 11, manufactured by Hakuyo Glass Co., Ltd., capacity: 110 mL) was charged with a target odorous substance to be used as a target sample. As the target odorous substance, muscone, guaiacol or p-cresol was used. As the muscone, a cotton ball soaked with 1 mg of muscone was used. As the guaiacol and p-cresol, 1 mL of a mineral oil (Sigma-Aldrich) solution in a concentration of 10 ppm was used. In a similar manner, a glass bottle was charged with a test substance to be used as a test sample. As the test sample, 5 mg of an ethyl vanillin powder, or 1 mL of a mineral oil (Sigma-Aldrich) solution of p-cresyl acetate, p-cresyl isobutyrate or p-methyl quinoline prepared to a concentration of 1,000 ppm was used.

The sensory test was performed by a single blind method by five to eight panelists. The target sample was first presented to each panelist, who was caused to replay on the odor intensity. Next, the test sample was presented for 2 minutes or until the odor could not be perceived. Thereafter, the target sample was presented again, and the panelist was caused to replay on the odor intensity. This series of operations was defined as one set, and the sensory test was carried out with four sets per day per panelist set as the upper limit. A recess of at least 10 minutes or more was provided between the sets.

The panelist was caused to plot the estimated intensity of the target odor on a straight line of 9.5 cm with both ends respectively provided with criteria "No odor" and "Strong odor". A distance (A) between the position of the target odor intensity plotted in the initial estimate and the end of "No odor", and a distance (B) between the position of the target odor intensity plotted in the second estimate and the end of "No odor" were obtained, so as to calculate percentage odor intensity of the initial estimate [B/A*100−100]. As this value is smaller, the intensity of the target odor perceived in the second estimate is suppressed stronger as compared with that in the initial estimate, namely, stronger cross-adaptation is induced. If this value is −100%, it means that the target odor was not perceived at all in the second estimate.

2) Results

The results of the sensory test are illustrated in FIG. 6. As for muscone, all the four odorous substances which had activated the OR5AN1 induced the cross-adaptation, and on the other hand, none of the four odorous substances which had not activated the OR5AN1 induced the cross-adaptation (FIG. 6A). In particular, PEA and Cis-3-hexenol which had activated the OR1A1, that is, a muscone receptor with low responsiveness, did not induce the cross-adaptation, and therefore, it was revealed that it is significant, for inducing cross-adaptation, to use a receptor having comparatively high responsiveness as a target. Besides, although Ambrettolide has an odor with similar nature to muscone, it did not induce the cross-adaptation. This suggests that the odor cross-adaptation is induced in a region on a peripheral side beyond the high-order brain region where the nature of an odor is recognized, and the principle of the present invention that the odor cross-adaptation is accountable at the level of olfactory receptors is thus supported.

The olfactory receptor having the highest responsiveness to the odor of guaiacol is the OR10G4 (FIG. 1). As a result of the sensory test, it was found that the cross-adaptation of the odor of guaiacol is induced by ethyl vanillin which activates the OR10G4 (FIG. 6B). On the other hand, the cross-adaptation of the odor of guaiacol is not induced by muscone which does not activate the OR10G4, and the cross-adaptation of ethyl vanillin is not induced by muscone. These results reveal that the principle that another substance recognized by an olfactory receptor highly reactive to a causative substance of a target odor induces the cross-adaptation of the target odor is applicable also to the OR10G4.

In order to verify that the principle is universal, a pair of p-cresol and the OR9Q2 was also examined whether or not the cross-adaptation was induced by another odorous substance which activates the OR9Q2. As a result, the cross-adaptation of the odor of p-cresol was induced by p-cresyl acetate, p-cresyl isobutyrate and p-methyl quinoline, which activate the p-cresol receptor OR9Q2 (FIG. 6C). On the other hand, muscone, which does not activate the OR9Q2, did not induce the cross-adaptation either for the odor of p-cresol or for the odors of p-cresyl acetate, p-cresyl isobutyrate and p-methyl quinoline.

These results prove the causal relationship between the odor cross-adaptation and the activation of an olfactory receptor, and for the first time, reveal the principle that the cross-adaptation of a target odor is induced by a substance capable of activating and desensitizing an olfactory receptor having high responsiveness to a causative substance of the target odor. On the basis of this principle, the present invention provides a novel method for identifying an odorous substance capable of suppressing a target odor based on the cross-adaptation using activation of response of an olfactory receptor as an index.

What is claimed is:

1. A method for selecting a substance that induces cross-adaptation of a target odor, comprising:
   (1) searching olfactory receptor polypeptides and identifying an olfactory receptor polypeptide that responds to a causative substance of the target odor;
   (2) expressing the olfactory receptor polypeptide in a recombinant cell genetically engineered to express the olfactory receptor polypeptide;
   (3) adding a test substance, which is different from the causative substance of the target odor, to the recombinant cell of part (2) that expresses the olfactory receptor polypeptide;
   (4) measuring the response of the olfactory receptor polypeptide of part (3) that is expressed by the recombinant cell to the test substance; and
   (5) selecting a test substance that activates the response of the olfactory receptor polypeptide as a substance that induces cross-adaptation of the target odor;
   wherein the olfactory receptor polypeptide is a rat, mouse or human olfactory receptor, or a polypeptide that has an amino acid sequence identity of at least 90% to a rat, mouse or human olfactory receptor and is responsive to the causative substance of the target odor.

2. The method according to claim 1, wherein the olfactory receptor polypeptide of part (1) is a human olfactory receptor polypeptide, or a polypeptide that has an amino acid sequence identity of at least 90% to a human olfactory receptor and is responsive to the causative substance of the target odor.

3. The method according to claim 2, wherein the olfactory receptor polypeptide is a human olfactory receptor polypeptide.

4. The method according to claim 1, wherein the response of the olfactory receptor polypeptide is measured in part (4) by measurement of an intracellular cAMP amount by ELISA or reporter gene assay, or by calcium imaging or an electrophysiological method.

5. The method according to claim 1, further comprising part (6) selecting a substance that induces the cross-adaptation of the target odor from substances selected in part (5) by a sensory test.

6. The method according to claim 1, wherein the target odor is a tobacco odor.

7. The method according to claim 1, wherein the target odor is a urine odor.

8. A method for selecting a substance that suppresses a target odor, comprising:
   (1) searching olfactory receptor polypeptides and identifying an olfactory receptor polypeptide that responds to a causative substance of the target odor;
   (2) expressing the olfactory receptor polypeptide that was identified in part (1) in a recombinant cell genetically engineered to express the olfactory receptor polypeptide;
   (3) adding a test substance that is different from the causative substance of the target odor, to the recombinant cell of part (2) that expresses the olfactory receptor polypeptide;
   (4) measuring the response of the olfactory receptor polypeptide to the test substance; and
   (5) selecting a test substance that activates the response of the olfactory receptor polypeptide as a substance that suppresses the target odor;
   wherein the olfactory receptor polypeptide is a rat, mouse or human olfactory receptor, or a polypeptide that has an amino acid sequence identity of at least 90% to a rat, mouse or human olfactory receptor and is responsive to the causative substance of the target odor.

9. The method according to claim 8, wherein the olfactory receptor polypeptide of part (1) is a human olfactory receptor polypeptide, or a polypeptide that has an amino acid sequence identity of at least 90% to a human olfactory receptor and is responsive to the causative substance of the target odor.

10. The method according to claim 9, wherein the olfactory receptor polypeptide is a human olfactory receptor polypeptide.

11. The method according to claim 8, wherein the response of the olfactory receptor polypeptide is measured in part (4) by measurement of an intracellular cAMP amount by ELISA or reporter gene assay, or by calcium imaging or an electrophysiological method.

12. The method according to claim 8, further comprising part (6) selecting a substance that suppresses the target odor from substances selected in (5) by a sensory test.

13. The method according to claim 8, wherein the target odor is a tobacco odor.

14. The method according to claim 8, wherein the target odor is a urine odor.

15. A method for selecting a substance that induces cross-adaptation of a target odor, comprising:
   (1) providing at least one or more types of olfactory receptor polypeptides that respond to a causative substance of the target odor;
   (2) expressing the one or more olfactory receptor polypeptides in a recombinant cell genetically engineered to express the one or more olfactory receptor polypeptides;
   (3) adding a test substance, which is different from the causative substance of the target odor, to the recombinant cell of part (2) that expresses the at least one or more types of olfactory receptor polypeptides;
   (4) measuring the response of the one or more types of olfactory receptor polypeptides to the test substance; and
   (5) selecting a test substance that activates the response of any of the at least one or more types of olfactory receptor polypeptides as a substance that induces the cross-adaptation of the target odor,
   wherein the target odor is a tobacco odor, and the at least one or more types of olfactory receptor polypeptides are at least one selected from the group consisting of a polypeptide consisting of the amino acid sequence of SEQ ID NO: 4, and a polypeptide having an identity of at least 90% to the amino acid sequence of SEQ ID NO: 4 and that responds having to a tobacco odor causative substance, or
   the target odor is a urine odor, and the at least one or more types of olfactory receptor polypeptides are at least one selected from the group consisting of a polypeptide consisting of an amino acid sequence as set forth in SEQ ID NO: 6, and a polypeptide having an identity of at least 90% to the amino acid sequence of SEQ ID NO: 6 and that responds to a urine odor causative substance.

16. The method according to claim 15, wherein the one or more olfactory receptor polypeptides consist of a polypeptide having the amino acid sequence of SEQ ID NO:4 or SEQ ID NO:6.

17. The method according to claim 15, wherein the one or more response of the olfactory receptor polypeptides is measured in part (4) by measurement of an intracellular cAMP amount by ELISA or reporter gene assay, or by calcium imaging or an electrophysiological method.

18. The method according to claim 15, further comprising part (6) selecting the substance inducing the cross-adaptation of the target odor from substances selected in part (5) by a sensory test.

19. A method for selecting a substance that suppresses a target odor, comprising:
(1) providing at least one or more types of olfactory receptor polypeptides that respond to a causative substance of the target odor;
(2) expressing the one or more olfactory receptor polypeptides in a recombinant cell genetically engineered to express the one or more olfactory receptor polypeptides;
(3) adding a test substance, which is different from the causative substance of the target odor, to the recombinant cell of part (2) that expresses the at least one or more types of olfactory receptor polypeptides;
(4) measuring the response of the one or more types of olfactory receptor polypeptides to the test substance; and
(5) selecting a test substance that activates the response of any of the at least one or more types of olfactory receptor polypeptides as a substance that suppresses the target odor,
wherein the target odor is a tobacco odor, and the at least one or more types of olfactory receptor polypeptides are at least one selected from the group consisting of a polypeptide consisting of an amino acid sequence as set forth in SEQ ID NO: 4, and a polypeptide having an identity of at least 90% to the amino acid sequence of SEQ ID NO:4 and that responds to a tobacco odor causative substance, or
the target odor is a urine odor, and the at least one or more olfactory receptor polypeptides are at least one selected from the group consisting of a polypeptide consisting of an amino acid sequence as set forth in SEQ ID NO: 6, and a polypeptide having an identity of at least 90% to the amino acid sequence of SEQ ID NO:6 and that responds to a urine odor causative substance.

20. The method according to claim 19, wherein the one or more olfactory receptor polypeptides consist of a polypeptide having the amino acid sequence set forth in SEQ ID NO:4 or SEQ ID NO:6.

21. The method according to claim 19, wherein the response of the one or more olfactory receptor polypeptides is measured in (5) is by measurement of an intracellular cAMP amount by ELISA or reporter gene assay, or by calcium imaging or an electrophysiological method.

22. The method according to claim 19, further comprising (6) selecting the substance suppressing the target odor from substances selected in (5) by a sensory test.

* * * * *

SEQUENCE LISTING

```
<160> NUMBER OF SEQ ID NOS: 6

<210> SEQ ID NO 1
<211> LENGTH: 936
<212> TYPE: DNA
<213> ORGANISM: Homo sapiens
<220> FEATURE:
<223> OTHER INFORMATION: DNA encoding human OR5AN1

<400> SEQUENCE: 1
atgactgggg gaggaaatat tacagaaatc acctatttca tcctgctggg attctcagat      60
tttcccagga tcataaaagt gctcttcact atattcctgg tgatctacat tacatctctg     120
gcctggaacc tctccctcat tgttttaata aggatggatt cccacctcca tacacccatg     180
tatttcttcc tcagtaacct gtccttcata gatgtctgct atatcagctc cacagtcccc     240
aagatgctct ccaacctctt acaggaacag caaactatca cttttgttgg ttgtattatt     300
cagtacttta tcttttcaac gatgggactg agtgagtctt gtctcatgac agccatggct     360
tatgatcgtt atgctgccat ttgtaacccc ctgctctatt catccatcat gtcacccacc     420
```

```
ctctgtgttt ggatggtact gggagcctac atgactggcc tcactgcttc tttattccaa    480
attggtgctt tgcttcaact ccacttctgt gggtctaatg tcatcagaca tttcttctgt    540
gacatgcccc aactgttaat cttgtcctgt actgacactt tctttgtaca ggtcatgact    600
gctatattaa ccatgttctt tgggatagca agtgccctag ttatcatgat atcctatggc    660
tatattggca tctccatcat gaagatcact tcagctaaag gcaggtccaa ggcattcaac    720
acctgtgctt tcatctaac agctgtttcc ctcttctata catcaggaat ctttgtctat     780
ttgagttcca gctctggagg ttcttcaagc tttgacagat ttgcatctgt tttctacact    840
gtggtcattc ccatgttaaa tcccttgatt tacagtttga ggaacaaaga aattaaagat    900
gccttaaaga ggttgcaaaa gagaaagtgc tgctga                             936
```

<210> SEQ ID NO 2
<211> LENGTH: 311
<212> TYPE: PRT
<213> ORGANISM: Homo sapiens
<220> FEATURE:
<223> OTHER INFORMATION: Human OR5AN1

<400> SEQUENCE: 2

```
Met Thr Gly Gly Gly Asn Ile Thr Glu Ile Thr Tyr Phe Ile Leu Leu
1               5                   10                  15

Gly Phe Ser Asp Phe Pro Arg Ile Ile Lys Val Leu Phe Thr Ile Phe
            20                  25                  30

Leu Val Ile Tyr Ile Thr Ser Leu Ala Trp Asn Leu Ser Leu Ile Val
        35                  40                  45

Leu Ile Arg Met Asp Ser His Leu His Thr Pro Met Tyr Phe Phe Leu
    50                  55                  60

Ser Asn Leu Ser Phe Ile Asp Val Cys Tyr Ile Ser Ser Thr Val Pro
65                  70                  75                  80

Lys Met Leu Ser Asn Leu Leu Gln Glu Gln Gln Thr Ile Thr Phe Val
                85                  90                  95

Gly Cys Ile Ile Gln Tyr Phe Ile Phe Ser Thr Met Gly Leu Ser Glu
            100                 105                 110

Ser Cys Leu Met Thr Ala Met Ala Tyr Asp Arg Tyr Ala Ala Ile Cys
        115                 120                 125

Asn Pro Leu Leu Tyr Ser Ser Ile Met Ser Pro Thr Leu Cys Val Trp
    130                 135                 140

Met Val Leu Gly Ala Tyr Met Thr Gly Leu Thr Ala Ser Leu Phe Gln
145                 150                 155                 160

Ile Gly Ala Leu Leu Gln Leu His Phe Cys Gly Ser Asn Val Ile Arg
                165                 170                 175

His Phe Phe Cys Asp Met Pro Gln Leu Leu Ile Leu Ser Cys Thr Asp
            180                 185                 190

Thr Phe Phe Val Gln Val Met Thr Ala Ile Leu Thr Met Phe Phe Gly
        195                 200                 205

Ile Ala Ser Ala Leu Val Ile Met Ile Ser Tyr Gly Tyr Ile Gly Ile
    210                 215                 220

Ser Ile Met Lys Ile Thr Ser Ala Lys Gly Arg Ser Lys Ala Phe Asn
225                 230                 235                 240

Thr Cys Ala Ser His Leu Thr Ala Val Ser Leu Phe Tyr Thr Ser Gly
                245                 250                 255

Ile Phe Val Tyr Leu Ser Ser Ser Gly Gly Ser Ser Phe Asp
            260                 265                 270
```

Arg Phe Ala Ser Val Phe Tyr Thr Val Val Ile Pro Met Leu Asn Pro
                275                 280                 285

Leu Ile Tyr Ser Leu Arg Asn Lys Glu Ile Lys Asp Ala Leu Lys Arg
        290                 295                 300

Leu Gln Lys Arg Lys Cys Cys
305                 310

<210> SEQ ID NO 3
<211> LENGTH: 936
<212> TYPE: DNA
<213> ORGANISM: Homo sapiens
<220> FEATURE:
<223> OTHER INFORMATION: DNA encoding human OR10G4

<400> SEQUENCE: 3
atgtccaacg ccagcctcgt gacagcattc atcctcacag gccttcccca tgccccaggg      60
ctggacgccc tcctctttgg aatcttcctg gtggtttacg tgctcactgt gctggggaac     120
ctcctcatcc tgctggtgat cagggtggat tctcacctcc acacccccat gtactacttc     180
ctcaccaacc tgtccttcat tgacatgtgg ttctccactg tcacggtgcc caaaatgctg     240
atgaccttgg tgtccccaag cggcagggct atctccttcc acagctgcgt ggctcagctc     300
tattttttcc acttcctggg gagcaccgag tgtttcctct acacagtcat gtcctatgat     360
cgctacttgg ccatcagtta cccgctcagg tacaccagca tgatgagtgg gagcaggtgt     420
gccctcctgg ccaccggcac ttggctcagt ggctctctgc actctgctgt ccagaccata     480
ttgactttcc atttgcccta ctgtggaccc aaccagatcc agcactactt ctgtgacgca     540
ccgcccatcc tgaaactggc ctgtgcagac acctcagcca acgtgatggt catctttgtg     600
gacattggga tagtggcctc aggctgcttt gtcctgatag tgctgtccta tgtgtccatc     660
gtctgttcca tcctgcggat ccgcacctca gatgggaggc gcagagcctt tcagacctgt     720
gcctcccact gtattgtggt cctttgcttc tttgttccct gtgttgtcat ttatctgagg     780
ccaggctcca tggatgccat ggatggagtt gtggccattt tctacactgt gctgacgccc     840
cttctcaacc tgttgtgta cacccctgaga acaaggagg tgaagaaagc tgtgttgaaa     900
cttagagaca aagtagcaca tcctcagagg aaataa                               936

<210> SEQ ID NO 4
<211> LENGTH: 311
<212> TYPE: PRT
<213> ORGANISM: Homo sapiens
<220> FEATURE:
<223> OTHER INFORMATION: Human OR10G4

<400> SEQUENCE: 4

Met Ser Asn Ala Ser Leu Val Thr Ala Phe Ile Leu Thr Gly Leu Pro
1               5                   10                  15

His Ala Pro Gly Leu Asp Ala Leu Leu Phe Gly Ile Phe Leu Val Val
            20                  25                  30

Tyr Val Leu Thr Val Leu Gly Asn Leu Leu Ile Leu Leu Val Ile Arg
        35                  40                  45

Val Asp Ser His Leu His Thr Pro Met Tyr Tyr Phe Leu Thr Asn Leu
    50                  55                  60

Ser Phe Ile Asp Met Trp Phe Ser Thr Val Thr Val Pro Lys Met Leu
65                  70                  75                  80

Met Thr Leu Val Ser Pro Ser Gly Arg Ala Ile Ser Phe His Ser Cys
                85                  90                  95

Val Ala Gln Leu Tyr Phe Phe His Phe Leu Gly Ser Thr Glu Cys Phe
            100                 105                 110

Leu Tyr Thr Val Met Ser Tyr Asp Arg Tyr Leu Ala Ile Ser Tyr Pro
            115                 120                 125

Leu Arg Tyr Thr Ser Met Met Ser Gly Ser Arg Cys Ala Leu Leu Ala
            130                 135                 140

Thr Gly Thr Trp Leu Ser Gly Ser Leu His Ser Ala Val Gln Thr Ile
145                 150                 155                 160

Leu Thr Phe His Leu Pro Tyr Cys Gly Pro Asn Gln Ile Gln His Tyr
                165                 170                 175

Phe Cys Asp Ala Pro Pro Ile Leu Lys Leu Ala Cys Ala Asp Thr Ser
            180                 185                 190

Ala Asn Val Met Val Ile Phe Val Asp Ile Gly Ile Val Ala Ser Gly
            195                 200                 205

Cys Phe Val Leu Ile Val Leu Ser Tyr Val Ser Ile Val Cys Ser Ile
210                 215                 220

Leu Arg Ile Arg Thr Ser Asp Gly Arg Arg Ala Phe Gln Thr Cys
225                 230                 235                 240

Ala Ser His Cys Ile Val Val Leu Cys Phe Phe Val Pro Cys Val Val
            245                 250                 255

Ile Tyr Leu Arg Pro Gly Ser Met Asp Ala Met Asp Gly Val Val Ala
            260                 265                 270

Ile Phe Tyr Thr Val Leu Thr Pro Leu Leu Asn Pro Val Val Tyr Thr
            275                 280                 285

Leu Arg Asn Lys Glu Val Lys Lys Ala Val Leu Lys Leu Arg Asp Lys
            290                 295                 300

Val Ala His Pro Gln Arg Lys
305                 310

<210> SEQ ID NO 5
<211> LENGTH: 945
<212> TYPE: DNA
<213> ORGANISM: Homo sapiens
<220> FEATURE:
<223> OTHER INFORMATION: DNA encoding human OR9Q2

<400> SEQUENCE: 5
atggctgaaa ggaattacac cgtagtgacg gagttcttcc ttactgcatt tactgaacat      60
ctccagtgga gggttcctct cttcctcata tttttgagtt tctatcttgc cactatgtta     120
gggaacacag gcatgatcct cctgatccgt ggcgatcgtc ggctccacac cccgatgtac     180
ttcttcctca gccaccttc cttggtggac atctgctact cgtccgccat catccctcag     240
atgctggctg tgctgtggga gcacggcaca accatctccc aggctcgctg tgcagctcag     300
ttcttcctct tcaccttctt tgcctccatc gactgctacc ttctggccat catggcctat     360
gaccgctaca cggccgtgtg ccagcccctg ctttatgtca ccatcataac cgagaaggcc     420
cgctggggcc tagtcactgg ggcttacgtt gctggttttt tcagtgcctt tgttcgaacg     480
gtcacagcct tcactctctc cttttgtgga aacaatgaga tcaacttcat tttctgtgac     540
ctccctcctc tattaaaact ctcctgtggg acagctacac tcaggaagt ggtgattatt     600 gtgtttgctc ttttcgtcat gcctgcctgt atcttggtga tcttggtatc ctacctgttt     660
atcattgtgg ccatcctgca gatccactct gctggaggcc gggccaagac cttctccacc     720
tgcgcctccc acctcactgc cgtcgctctt ttctttggca ccctcatctt catgtacctg     780

```
cgagacaaca caggccagtc ctccgaggga gaccgagtgg tgtctgtgct ctacacggtg    840
gtgaccccaa tgctgaatcc ccttatctat agcctgagaa acaaggaggt aaaagaggcc    900
actaggaaag ccctgagcaa atcaaagcct gctagaagac cctaa                    945
```

<210> SEQ ID NO 6
<211> LENGTH: 314
<212> TYPE: PRT
<213> ORGANISM: Homo sapiens
<220> FEATURE:
<223> OTHER INFORMATION: Human OR9Q2

<400> SEQUENCE: 6

```
Met Ala Glu Arg Asn Tyr Thr Val Val Thr Glu Phe Phe Leu Thr Ala
1               5                   10                  15

Phe Thr Glu His Leu Gln Trp Arg Val Pro Leu Phe Leu Ile Phe Leu
            20                  25                  30

Ser Phe Tyr Leu Ala Thr Met Leu Gly Asn Thr Gly Met Ile Leu Leu
        35                  40                  45

Ile Arg Gly Asp Arg Arg Leu His Thr Pro Met Tyr Phe Phe Leu Ser
50                  55                  60

His Leu Ser Leu Val Asp Ile Cys Tyr Ser Ser Ala Ile Ile Pro Gln
65                  70                  75                  80

Met Leu Ala Val Leu Trp Glu His Gly Thr Thr Ile Ser Gln Ala Arg
                85                  90                  95

Cys Ala Ala Gln Phe Phe Leu Phe Thr Phe Ala Ser Ile Asp Cys
            100                 105                 110

Tyr Leu Leu Ala Ile Met Ala Tyr Asp Arg Tyr Thr Ala Val Cys Gln
        115                 120                 125

Pro Leu Leu Tyr Val Thr Ile Ile Thr Glu Lys Ala Arg Trp Gly Leu
130                 135                 140

Val Thr Gly Ala Tyr Val Ala Gly Phe Phe Ser Ala Phe Val Arg Thr
145                 150                 155                 160

Val Thr Ala Phe Thr Leu Ser Phe Cys Gly Asn Asn Glu Ile Asn Phe
                165                 170                 175

Ile Phe Cys Asp Leu Pro Pro Leu Leu Lys Leu Ser Cys Gly Asp Ser
            180                 185                 190

Tyr Thr Gln Glu Val Val Ile Val Phe Ala Leu Phe Val Met Pro
        195                 200                 205

Ala Cys Ile Leu Val Ile Leu Val Ser Tyr Leu Phe Ile Ile Val Ala
210                 215                 220

Ile Leu Gln Ile His Ser Ala Gly Gly Arg Ala Lys Thr Phe Ser Thr
225                 230                 235                 240

Cys Ala Ser His Leu Thr Ala Val Ala Leu Phe Phe Gly Thr Leu Ile
                245                 250                 255

Phe Met Tyr Leu Arg Asp Asn Thr Gly Gln Ser Ser Glu Gly Asp Arg
            260                 265                 270

Val Val Ser Val Leu Tyr Thr Val Val Thr Pro Met Leu Asn Pro Leu
        275                 280                 285

Ile Tyr Ser Leu Arg Asn Lys Glu Val Lys Glu Ala Thr Arg Lys Ala
290                 295                 300

Leu Ser Lys Ser Lys Pro Ala Arg Arg Pro
305                 310
```